(12) United States Patent
Awasthi et al.

(10) Patent No.: US 10,953,113 B2
(45) Date of Patent: Mar. 23, 2021

(54) IMAGING AGENTS AND METHODS OF USE

(71) Applicant: The Board of Regents of the University of Oklahoma, Norman, OK (US)

(72) Inventors: Vibhudutta Awasthi, Edmond, OK (US); Hailey Houson, Oklahoma City, OK (US); Gregory Nkepang, Oklahoma City, OK (US)

(73) Assignee: THE BOARD OF REGENTS OF THE UNIVERSITY OF OKLAHOMA, Norman, OK (US)

( * ) Notice: Subject to any disclaimer, the term of this patent is extended or adjusted under 35 U.S.C. 154(b) by 0 days.

(21) Appl. No.: 16/465,887

(22) PCT Filed: Nov. 30, 2017

(86) PCT No.: PCT/US2017/063994
§ 371 (c)(1),
(2) Date: May 31, 2019

(87) PCT Pub. No.: WO2018/102574
PCT Pub. Date: Jun. 7, 2018

(65) Prior Publication Data
US 2020/0078477 A1 Mar. 12, 2020

Related U.S. Application Data

(60) Provisional application No. 62/429,169, filed on Dec. 2, 2016.

(51) Int. Cl.
| | |
|---|---|
| *A61K 51/00* | (2006.01) |
| *A61M 36/14* | (2006.01) |
| *A61K 51/04* | (2006.01) |
| *C07H 1/00* | (2006.01) |
| *C07H 7/033* | (2006.01) |

(52) U.S. Cl.
CPC .......... *A61K 51/0491* (2013.01); *C07H 1/00* (2013.01); *A61K 2123/00* (2013.01); *C07H 7/033* (2013.01)

(58) Field of Classification Search
CPC .. A61K 51/0491; A61K 2123/00; C07H 1/00; C07H 7/033
USPC ...................................................... 424/1.73
See application file for complete search history.

(56) References Cited

U.S. PATENT DOCUMENTS

| | | |
|---|---|---|
| 4,946,668 A | 8/1990 | Daddona et al. |
| 2005/0152835 A1* | 7/2005 | Pak .................... A61K 51/0402 424/1.11 |
| 2005/0232861 A1 | 10/2005 | Buchanan et al. |
| 2006/0083678 A1* | 4/2006 | Frangioni ............ C07D 317/30 424/1.11 |
| 2006/0127309 A1 | 6/2006 | Raffel et al. |
| 2008/0138281 A1 | 6/2008 | Sugiyama et al. |

OTHER PUBLICATIONS

Meng et al. Nucl. Med. Biol. 2015, 42, 608-613. (Year: 2015).*
Merbough et al. Carbohydrate Res. 2001, 336, 75-78. (Year: 2001).*
Buriova et al. J. Radioanal. Nuc. Chem. 2005, 264, 595-602. (Year: 2005).*
Marsh Carbohydrate Res. 153 (1986) 119-131. (Year: 1986).*
Dai et al. Fibers and Polymers 2015, 16, 319-325.*
Abouzied MM, Crawford ES, Nabi HA. 18F-FDG imaging: pitfalls and artifacts. J Nucl Med Technol. Sep. 2005; 33(3):145-55.
Bender D, Munk OL, Feng HQ, Keiding S. Metabolites of (18)F-FDG and 3-O-(11)C-methylglucose in pig liver. J Nucl Med. Nov. 2001, pp. 1673-1678.
Hariprasad Gali et al., Evaluation of 18F-FGA PET/CT for specific imaging of necrotic tissue in a mouse model of coronary artery ligation, J Nucl Med May 1, 2020 vol. 61 No. supplement 1 228.
Houson HA, Nkepang GN, Hedrick AF, Awasthi V. Imaging of isoproterenol-induced myocardial injury with 18F labeled fluoroglucaric acid in a rat model. Nuclear Medicine and Biology. Apr. 2018;59:9-15.
Vanina Isnardi et al., Is [99mTc]glucarate uptake mediated by fructose transporter GLUT-5?, Nuclear Medicine and Biology vol. 39, Issue 8, Nov. 2012, pp. 1226-1231.
Leung K. [18F]Fluoro-2-deoxy-2-D-glucose [18F]FDG. Oct. 1, 2004 [Updated Jan. 12, 2005]. In: Molecular Imaging and Contrast Agent Database (MICAD).
Liu Z, Barrett HH, Stevenson GD, et al. High-resolution imaging with (99m)Tc-glucarate for assessing myocardial injury in rat heart models exposed to different durations of ischemia with reperfusion. J Nucl Med. 2004;45(7):1251-1259.
Orlandi, Cesare & Crane, P & Edwards, D & Platts, Steve & Bernard, L & Lazewatsky, Joel & Thoolen, M. (1991). Early scintigraphic detection of experimental myocardial infarction in dogs with technetium-99m-glucaric acid. Journal of nuclear medicine : official publication, Society of Nuclear Medicine. 32. 263-8.
Infarct-Avid Imaging Agents, Section III, Chapter 10—Technetium-99m Glucarate, Raymond Taillefer (1999). pp. 197-209.
Written Opinion; Singapore Application No. 11201905611T; Intellectual Property Office of Singapore; dated Jul. 14, 2020; 6 pages.
International Search Report and Written Opinion for International Application No. PCT/US17/63994; dated Mar. 29, 2018; 13 pages.
Houson, Hailey, et al.; Use of Novel PET Agent F-18-labeled Glucaric Acid to Image Isoproterenol-Induced Myocardial Injury; The Journal of Nuclear Medicine; https://jnm.snmjournals.org/content/58/supplement_1/166; May 2017, vol. 58, Issue supplement 1/166; 2 pages.

(Continued)

*Primary Examiner* — Michael G. Hartley
*Assistant Examiner* — Sean R Donohue
(74) *Attorney, Agent, or Firm* — Dilworth IP, LLC

(57) ABSTRACT

An imaging agent and a method of its use for imaging a necrosis in a tissue of a subject. The imaging method may be positron emission tomography (PET). In at least one embodiment the imaging agent comprises 2-deoxy-2-[$^{18}$F] fluoroglucaric acid ($^{18}$F-FGA), or a pharmaceutically-acceptable salt thereof. The imaging agent may be disposed in a pharmaceutically-acceptable excipient, carrier, diluent, or vehicle. The imaging agent may be contained within a kit. The disclosure includes in at least one embodiment a method of preparing a radiopharmaceutical such as $^{18}$F-FGA for use in imaging.

8 Claims, 11 Drawing Sheets

(56) References Cited

OTHER PUBLICATIONS

European Search Report for EP Application No. 17875502.1; dated Jun. 16, 2020, 4 pages.
Ballinger, J.R., et al.; "Stable Kit Formulation of Technetium-99m Glucarate"; Apl. Radiat. Isot. 42:4 (1991) 405-406.
Orlandi, C., et al.; "Early Scintigraphic Detection of Experimental Myocardial Infarction in Dogs with Technetium-99m-Glucaric Acid"; The Journal of Nuclear Medicine 32:2 (1991) 263-268.
Willerson, J.T.; "Detection of Acute Myocardial Infarcts by Infarct-Avid Imaging"; The Journal of Nuclear Medicine; 32:2 (1991) 269-271.
Yaoita, H., et al.; "Localization of Technetium-99m-Glucarate in Zones of Acute Cerebral Injury"; The Journal of Nuclear Medicine 32:2 (1991) 272-278.
Ohtani, H., et al.; "Comparison of Technetium-99m-Glucarate and Thallium-201 for the Identification of Acute Myocardial Infarction in Rats"; The Journal of Nuclear Medicine 33:11 (1992) 1988-1993.
Pak, K.Y., et al.; "An Instant Kit Method for Labeling Antimyosin Fab' with Technetium-99m: Evaluation in an Experimental Myocardial Infarct Model"; The Journal of Nuclear Medicine 33:1 (1992) 144-149.
Pak, K.Y., et al.; "Labeling and Stability of Radiolabeled Antibody Fragments by a Direct 99m Tc-labeling Method"; Nucl. Med. Biol. 19:6 (1992) 669-677.
Ballinger, J.R., et al.; "Effect of Hypoxia on the Accumulation of Technetium-99m-Glucarate and Technetium-99m-Gluconate by Chinese Hamster Ovary Cells in Vitro"; The Journal of Nuclear Medicine 34:2 (1993) 242-245.
Yaoita, H., et al.; "Distribution of Deoxyglucose and Technetium-99m-Glucarate in the Acutely Ischemic Myocardium"; The Journal of Nuclear Medicine 34:8 (1993) 1303-1308.
Khaw, B., et al.; "What is new in Infarct Imaging?"; American Society of Nuclear Cardiology 2:3 (1995) 3 pages.
Vural, I., et al.; "Can Tc-99m Glucarate Also Recognize Diffuse Myocardial Necrosis?"; J. Nucl. Med 36 (1995) 1 page.
Khaw, B.; "Early Detection of Myocardial Injury and Infarction"; Proceedings of the 43rd Annual Meeting of the Society Nuclear Medicine, Denver, CO; Jun. 3-5, 1996; 4 pages.
Rammohan, R., et al.; "Subnuclear Localization of Tc-99m Glucarate in Necrotic Myocardium"; J. Nucl. Med. 37 (1996) 1 page.
Beanlands, R.S.B., et al.; "Differentiation of myocardial ischemia and necrosis by technetium 99m glucaric acid kinetics"; American Society of Nuclear Cardiology 4:4 (1997) 274-282.
Gerson, Myron C., et al.; "Technetium 99m glucarate: What will be its clinical role?"; Journal of Nuclear Cardiology 4:4 (1997) 336-340.
Khaw, B., et al.; "Avidity of technetium 99m glucarate for the necrotic myocardium: In vivo and in vitro assessment"; Journal of Nuclear Cardiology 4:4 (1997) 283-290.
Molea, N., et al.; "Biodistribution Pharmacokinetics and Dosimetry of 99mTc-D-Glucaric Acid in Humans"; Radioactive Isotopes in Clinical Medicine and Research XXII (1997) 359-364.
Narula, J., et al.; "Very Early Noninvasive Detection of Acute Experimental Nonreperfused Myocardial Infarction With 99mTc-Labeled Glucarate"; Circulation 95:6 (1997) 1577-1584.
Pak, C., et al.; "Amiscan(TM) (Tc-99m glucarate)—A novel delineator of acute myocardial infarction: From Laboratory to Clinic"; Molecular Targeting Technology, Inc.; 1997; 5 pages.
Petrov, A.D., et al.; "Targeting human breast tumour in xeno-grafted SCID mice with 99Tcm-glucarate"; Nuclear Medicine Communications 18 (1997) 241-251.
Botvinick, E.; "Hot Spot Imaging"; Journal of Nuclear Cardiology (1998) 1 page.
Khaw, B., et al.; "New Approaches to Infarct-Avid Imaging"; New Developments in Cardiac Nuclear Imaging (1998) 171-202.
Khaw, B.; "New Methods in Nuclear Cardiac Imaging Infarct Avid Agents"; American Society of Nuclear Cardiology (1998) 9 pages.
Khaw, B., et al.; "Can the Uptake Ratios of TC-99m Glucarate in Acute Myocardial Infarction be Affected by the Glycemic State? Biodistribution in Fasted, Non-Fasted and Insulin Infected Mice"; J Nucl Med 40 (1999) 1 page.
Khaw, B.; "New Infarct Avid Imaging Agents"; Society of Nuclear Medicine (1999) 6 pages.
Liu, Z., et al.; "TC-99m Glucarate can Detect Myocardial Necrosis Early After Injury Due to Severe Ischemia with Reperfusion"; Journal Nuclear Medicine; Proceedings of the 46th Annual Meeting (1999) 1 page.
Mariani, G., et al.; "Detection of Acute Myocardial Infarction by 99mTC-Labeled D-Glucaric Acid Imaging in Patients with Acute Chest Pain"; The Journal of Nuclear Medicine 40:11 (1999) 1832-1839.
Taillefer, R.; "Technetium-99m Glucarate"; Section III, Infarct-Avid Imaging Agents (1999) 197-209.
Johnson, L.L., et al.; "Technetium-99m glucarate uptake in a swine model of limited flow plus increased demand"; Journal of Nuclear Cardiology 7:6 (2000) 590-598.
Wiersema, A.M., et al.; "Early assessment of skeletal muscle damage after ischaemia-reperfusion injury using Tc-99m-glucarate"; Cardiovascular Surgery 8:3 (2000) 186-191.
Arteaga De Murphy, C., et al.; "99mTc-glucarate for detection of isoproterenol-induced myocardial infarction in rats"; International Journal of Pharmaceutics 233:1 (2002) 29-34.
Khaw, B., et al.; "Indium 111 antimyosic and Tc-99m glucaric acid for noninvasive identification of oncotic and apoptotic myocardial necrosis"; Journal of Nuclear Cardiology 9:5 (2002) 471-481.
Ballinger, J.R., et al.; "Accumulation of technetium-99m glucarate: in vitro cell cultures and in vivo tumour models"; Nuclear Medicine Communications 24 (2003) 597-606.
Okada, D.R., et al.; "Myiocardial kinetics of Tc-99m glucarate in low flow, hypoxia, and aglycemia"; Journal of Nuclear Cardiology 10:2 (2003) 168-176.
Liu, Z., et al.; "99mTc glucarate high-resolution imaging of drug senstive and drug resistant human breast cancer xenografts in SCID mice"; Nucl Med Commun. 25:7 (2004) 711-720.
Liu, Z., et al.; "High-Resolution Imaging with 99m Tc-Glucarate for Assessing Myocardial Injury in Rat Heart Models Exposed to Different Durations of Ischemia with Reperfusion"; The Journal of Nuclear Medicine 45:7 (2004) 1251-1259.
Okada, D.R., et al.; "Early Detection of Infarct in Reperfused Canine Myocardium Using 99mTc-Glucarate"; J Nucl Med 45:4 (2004) 655-664.
Gambini, J.P., et al.; "99mTc-Glucarate as a potential novel tracer of lunh cancer lesions"; Alasbimm Journal; Year 9, No. 34; Article No. AJ34-3 (2006) 6 pages.
Perek, N., et al.; "Could 99mTc-glucarate be used to evaluate tumour necrosis?"; Eur J. Nucl Med Mol Imaging 35 (2008) 1290-1298.
Gambini, J.P., et al.; "Is 99mTc Glucarate a tracer of tumor necrosis? Comparison with 18F-FDG-PET in an animal model of breast cancer and preliminary clinical experience in oncology patients."; Alasbimm Journal; Year 10, No. 40 (2008) 8 pages.
Liu, Z., et al.; "Evaluating the protective role of ischaemic preconditioning in rat hearts using a stationary small-animal SPECT imager and 99mTC-glucarate"; Nucl Med Commun. 29:2 (2008) 120-128.
Cheng, D., et al.; "A Brief Evaluation of Tumor Imaging in Mice with 99mTc-glucarate Including a Comparison with 18F-FDG"; Current Radiopharmaceuticals 4 (2011) 5-9.
Gambini, J.P., et al.; "Evaluation of 99mTc-glucarate as a breast cancer imaging agent in a xenograft animal model"; Nuclear Medicine and Biology 38 (2011) 255-260.
Choudhury, P.S., et al.; "99mTc Glucarate as a Potential Radiopharmaceutical Agent for Assessment of Tumor Viability: From Bench to the Bed Side"; World Journal of Nuclear Medicine 11:2 (2012) 47-56.
Isnardi, V., et al.; "Is [99mTc]glucarate uptake mediated by fructose transporter GLUT-5?"; Nuclear Medicine and Biology 39 (2012) 1226-1231.

(56) References Cited

OTHER PUBLICATIONS

Wyffels, L., et al.; "Detection of Myocardial Ischemia-Reperfusion Injury Using a Fluorescent Near-Infrared Zinc(II)-Dipicolylamine Probe and 99mTc Glucarate"; Molecular Imaging 11:3 (2012) 187-196.

Meng, L., et al.; "Investigations of 99mTc-labeled glucarate as a SPECT radiotracer for non-small cell lung cancer (NSCLC) and potential tumor uptake mechanism"; Nuclear Medicine and Biology 42 (2015) 608-613.

* cited by examiner

Scheme 1

Scheme 2

IMAGING AGENTS AND METHODS OF USE

CROSS-REFERENCE TO RELATED APPLICATIONS

The present application is a national stage application of a PCT application having International Application No. PCT/US2017/063994, filed Nov. 30, 2017, which claims priority to U.S. Provisional Application having U.S. Ser. No. 62/429,169, filed Dec. 2, 2016, which claims the benefit under 35 U.S.C. 119(e), the disclosure of which is hereby expressly incorporated herein by reference.

GOVERNMENT SUPPORT

Not applicable.

BACKGROUND

Myocardial infarction (MI) is a leading cause of death in the United States and in most developed nations throughout the world. MI can be an acute manifestation, due to a mismatch in oxygen demand and supply to the cardiac tissue, or chronic heart failure attributed mostly to the left ventricular dysfunction. Acute MI requires rapid diagnosis for effective and timely thrombolytic therapy, whereas chronic heart failure needs accurate assessment of myocardial viability and localization of dysfunctional region prior to revascularization. Non-invasive nuclear imaging procedures exhibit immense diagnostic value in evaluation of patients with MI. Depending on the parameter assessed, these procedures are categorized as perfusion imaging for assessing coronary blood flow (e.g., $^{99m}$Tc-sesta-methoxy-isobutylisonitrile ($^{99m}$Tc-sestamibi) and $^{201}$Tl—TlCl$_2$) or metabolic imaging for quantifying cardiac metabolism (e.g., $^{18}$F-FDG (2-deoxy-2-[$^{18}$F]fluoro-D-glucose) and $^{11}$C-acetate). A third nuclear technique is the infarct-avid scintigraphy. Infarct-avid scintigraphy is a relatively less utilized procedure, because an effective radiopharmaceutical is currently unavailable. Perfusion imaging tests rely on imaging agents which are taken up by living tissues, thus the areas of infarct or necrosis are indicated only indirectly. Perfusion imaging cannot differentiate between areas of low flow, ventricular thinning, and attenuation. Additionally, high liver uptake creates imaging artifacts which make image interpretation difficult. Finally, perfusion scans cannot discriminate between ischemic and necrotic regions because both show reduced perfusion.

In contrast to perfusion imaging agents, infarct-avid agents accumulate in the site of injury. Infarct-avid scintigraphy exhibits less background and enhanced signal-to-noise ratio, as there is no uptake by normal myocardium. The two currently usable infarct-avid agents are $^{99m}$Tc-pyrophosphate (PyP) and $^{111}$In-antimyosin. They are called 'hot-spot' markers because of their tendency to accumulate in regions of infarcted myocardium. However, these agents have drawbacks. For example, regarding $^{111}$In-antimyosin, deficiencies include the relatively poor radionuclidic characteristics of $^{111}$In, delayed blood clearance, and pronounced hepatic uptake. On the other hand, PyP lacks specificity (64%), and exhibits poor sensitivity (40%) for subendocardial infarct detection. Moreover, PyP is not very useful in early diagnosis of acute MI as its uptake only becomes positive after 24-48 h of infarction. In addition to PyP and anti-myosin, a $^{99m}$Tc-labeled analog of glucaric acid has been investigated for the acute localization of MI. Its avidity towards infarct is based on its binding to highly basic histones that are exposed in injured tissue. Single photon emission computed tomography (SPECT) with $^{99m}$Tc-glucarate has been shown to be specific for the presence of myocardial necrosis, and has been able to address most drawbacks of PyP and $^{111}$In-antimyosin. However, a shortcoming of $^{99m}$Tc-glucarate used in SPECT is that the $^{99m}$Tc is only complexed with, not covalently linked to, the glucarate molecule. As a result over time the $^{99m}$Tc may dissociate from glucarate and transchelate to other circulating ligands resulting in a less accurate diagnosis.

Positron emission tomography (PET) provides improved resolution and sensitivity of detection as compared to SPECT. Moreover, PET is less prone to image artifacts and attenuation. With recent introduction of $^{18}$F-labeled perfusion agents such as Flurpiridaz, myocardial perfusion imaging (MPI) with PET is likely to complement or supplant traditional SPECT/PET protocols for objective decision-making in the management of MI patients. However, there is currently no PET agent for specifically imaging myocardial infarcts.

Like acute MI, the pathology of brain stroke also involves the development of necrosis very early post-ictus. Brain stroke is the second most common cause of death worldwide, with considerable disability among survivors. Stroke-survivors exhibit considerable disability for a prolonged period, which totaled about 113 million disability-adjusted life years in 2013. Approximately 80% of brain strokes are from ischemic infarction due to thrombotic or embolic cerebrovascular occlusion, and the rest are categorized as hemorrhagic stroke. After transient ischemic attack (TIA) or minor stroke, the risk of further stroke reaches as high as 30% within the first month in some subgroups. Stroke consumes 2-4% of total health-care costs worldwide, but in developed countries the figure exceeds 4%. Current management of stroke patients is aimed at preventing the progression of at-risk cerebral tissue towards infarction by restoring blood supply to ischemic but viable tissue (a.k.a. penumbra). The timing of treatment with respect to the type and stage of evolution of stroke critically determines the treatment success. Neuroimaging based on diffusion-perfusion mismatch in magnetic resonance (MR) or computed tomography (CT) images is routinely employed for discerning non-viable and viable tissue and optimize treatment in brain stroke patients. However, diffusion-perfusion mismatch is not always a reliable indicator of salvageable tissue because some lesions show acute reversal, whereas others fail to transition into infarct. There also exists lack of consensus on thresholds employed for delineating diffusion and perfusion deficits in MR or CT images. Thus, infarct imaging would provide significant assistance in diagnosis and treatment planning of brain stroke.

BRIEF DESCRIPTION OF THE DRAWINGS

Several embodiments of the present disclosure are hereby illustrated in the appended drawings. It is to be noted however, that the appended drawings only illustrate several typical embodiments and are therefore not intended to be considered limiting of the scope of the inventive concepts disclosed herein. The patent or application file contains at least one drawing executed in color. Copies of this patent or patent application publication with color drawing(s) will be provided by the Office upon request and payment of the necessary fee.

DETAILED DESCRIPTION

Figure 1:
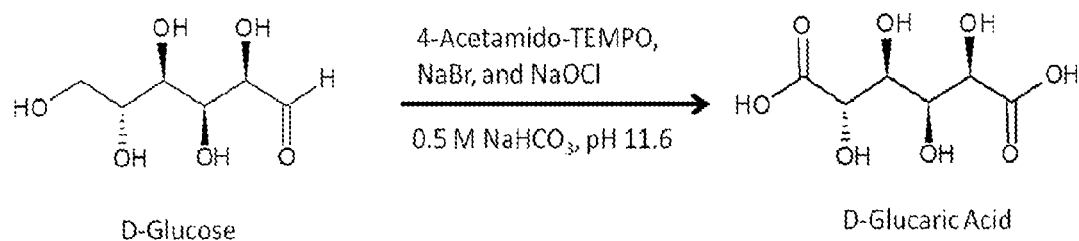
FIG. 1 shows an oxidation reaction of glucose to glucaric acid (Scheme 1) using a TEMPO/NaBr/NaOCl system.

The present disclosure is directed to imaging agents which localize in necrotic tissue (e.g., myocardial and cerebral, or any other organ system with necrotic tissue). The imaging agents can thus be used to diagnose acute areas of infarction or necrosis through infarct-avid imaging methods, such as PET. In at least one embodiment the imaging agent is 2-deoxy-2-[$^{18}$F]fluoroglucaric acid ($^{18}$F-labeled glucaric acid, also referred to herein as, [$^{18}$F]fluoroglucaric acid, $^{18}$F-FGA, FGA, and F-18-FGA). PET is known to be an extremely sensitive technique for high resolution functional imaging of blood flow, glucose metabolism, and oxygen extraction in myocardial infarction and brain stroke. However, it has not been possible to directly visualize infarcted or necrotic tissue. Prior to the presently disclosed novel compounds, there was no infarct-avid imaging agent available for longitudinal PET imaging to assess growth of infarct area. As explained below $^{18}$F-FGA is the first infarct-avid PET agent with demonstrated effectiveness for infarct imaging which has been shown to delineate MI and brain stroke. $^{18}$F-FGA undergoes rapid clearance from the body and does not accumulate in normal tissues which would otherwise create imaging artifacts and/or high background signal. $^{18}$F-FGA targets the early cellular changes that occur in infarction independent of electrical signaling or serum protein levels. Hence, it can be used to diagnose infarcted tissue early post-MI or post-ictus (e.g., brain stroke), or due to traumatic brain injury for example. $^{18}$F-FGA can also be used as an imaging agent to detect necrotic tissue in the breast, prostate, colon, kidney, spleen, limb, and lung, as well as other tissues and organs which may develop infarcts and/or necroses, including cancer.

Before further describing various embodiments of the compositions and methods of the present disclosure in more detail by way of exemplary description, examples, and results, it is to be understood that the embodiments of the present disclosure are not limited in application to the details of methods and compositions as set forth in the following description. The description provided herein is intended for purposes of illustration only and is not intended to be construed in a limiting sense. The inventive concepts of the present disclosure are capable of other embodiments or of being practiced or carried out in various ways. As such, the language used herein is intended to be given the broadest possible scope and meaning; and the embodiments are meant to be exemplary, not exhaustive, and it is not intended that the present disclosure be limited to these particular embodiments. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description. It is intended that all alternatives, substitutions, modifications and equivalents apparent to those having ordinary skill in the art are included within the scope of the present disclosure. All of the compositions and methods of production and application and use thereof disclosed herein can be made and executed without undue experimentation in light of the present disclosure. Thus, while the compositions and methods of the present disclosure have been described in terms of particular embodiments, it will be apparent to those of skill in the art that variations may be applied to the formulations, compounds, or compositions and/or methods and in the steps or in the sequence of steps of the method described herein without departing from the spirit and scope of the inventive concepts of the present disclosure.

All patents, published patent applications, and non-patent publications mentioned in the specification are indicative of the level of skill of those skilled in the art to which the present disclosure pertains. Further, all patents, published patent applications, and non-patent publications referenced in any portion of this application, including but not limited to U.S. Provisional Application No. 62/429,169, filed Dec. 2, 2016, are herein expressly incorporated by reference in their entirety to the same extent as if each individual patent or publication was specifically and individually indicated to be incorporated by reference.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example. By way of further example, the range 1 wt % to 99 wt % is intended to include any sub-range therein, although that sub-range may not be explicitly designated herein. For example, since the range 1 wt % to 99 wt % includes all integers from 1 to 99, the sub-ranges therein include any range having a minimum value of 1 wt % to 98 wt % and any maximum value of 2 wt % to 99 wt %, such as but not limited to, 5 wt % to 75 wt %, 10 wt % to 50 wt %, or 15 wt % to 40 wt %.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, a temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance (e.g., reaction) occurs at least 90% of the time, or at least 95% of the time, or at least 99% of the time, or to at least 90% completion, or to at least 95% completion, or to at least 99% completion.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

The term "pharmaceutically acceptable" refers to compounds and compositions which are suitable for administration to humans and/or animals without undue adverse side effects such as toxicity, irritation and/or allergic response commensurate with a reasonable benefit/risk ratio. The compounds of the present disclosure may be combined with one or more pharmaceutically-acceptable excipients, carriers, vehicles, and/or diluents which may improve solubility, deliverability, dispersion, stability, and/or conformational integrity thereof.

By "biologically active" is meant the ability to modify or affect the physiological system of an organism without reference to how the active agent has its physiological effects.

As used herein, "pure," or "substantially pure" means an object species (e.g., an imaging agent) is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species (e.g., an imaging agent) is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

The terms "subject" and "patient" are used interchangeably herein and will be understood to refer to a warm blooded animal, particularly a mammal, and more particularly, a human. Animals which fall within the scope of the term "subject" as used herein include, but are not limited to, dogs, cats, rats, mice, guinea pigs, chinchillas, horses, goats, ruminants such as cattle, sheep, swine, poultry such as chickens, geese, ducks, and turkeys, zoo animals, Old and New World monkeys, and non-human primates.

"Treatment" refers to therapeutic or diagnostic treatments. "Prevention" refers to prophylactic or preventative treatment measures. The term "treating" refers to administering the composition to a patient for therapeutic or diagnostic purposes.

The terms "therapeutic composition," "pharmaceutical composition," and "diagnostic composition" refer to an active agent-containing composition (a composition comprising e.g., an imaging agent, for example, $^{18}$F-FGA) that may be administered to a subject by any method known in the art or otherwise contemplated herein, wherein administration of the composition brings about an effect as described elsewhere herein. In addition, the compositions of the present disclosure may be designed to provide delayed, controlled, extended, and/or sustained release using formulation techniques which are well known in the art.

The term "effective amount" refers to an amount of an active agent (e.g., an imaging agent) as defined herein (e.g., $^{18}$F-FGA) which is sufficient to exhibit a detectable effect or result without excessive adverse side effects (such as toxicity, irritation and allergic response) commensurate with a reasonable benefit/risk ratio when used in the manner of the inventive concepts. The effective amount for a patient will depend upon the type of patient, the patient's size and health, the nature and severity of the condition to be treated or diagnosed, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

Where used herein, for at least some embodiments, the term "buffering agent" refers to any alkaline buffer (such as but not limited to sodium carbonate, ammonia-ammonium chloride, or N-cyclohexyl-3-aminopropanesulfonic acid) of sufficient strength (e.g., 0.1M to 2M) to be able to maintain a desired pH range (e.g., pH 9-12) during the reaction.

Where used herein, for at least some embodiments, the term "oxidizing agent" refers to 2,2,6,6-tetramethylpiperidine 1-oxyl radical (TEMPO) or a derivative thereof. Derivatives of TEMPO include but are not limited to 4-hydroxy-TEMPO, TEMPO methacrylate, 4-Oxo-TEMPO, 4-amino-TEMPO, 4-acetamido-TEMPO, 4-carboxy-TEMPO, 4-hydroxy-TEMPO benzoate, 4-(2-Iodoacetamido)-TEMPO, 4-Maleimido-TEMPO, 4-Isothiocyanato-TEMPO, 4-(2-Bromoacetamido)-TEMPO, 4-methoxy-TEMPO, 4-Cyano-TEMPO, 4-amino-4-carboxy-TEMPO, 4-Phosphonooxy-TEMPO hydrate, and 2,2,6,6-tetramethyl-4-(methylsulfonyloxy)-1-piperidinooxy. The TEMPO or TEMPO derivatives may be free compounds or linked to bead, resins, or polymers. Other oxidizing agents that could be used include but are not limited to, hydrogen peroxide, sodium hypochlorite, calcium hypochlorite, ozone, nitric acid, permanganate compounds, halogens, and metal-catalyzed oxidation agents. Oxidation may also occur via electrochemical oxidation in the presence or absence of a chemical catalyst, via gold or other nanoparticles which mimic peroxidase activity, via enzymatic oxidation or by enzymes such as glucose oxidase, or via any other physicochemical means or condition by which glucose could be forced to undergo electron donation. In fact, the oxidizing conditions of the present disclosure are intended to include any condition capable of oxidizing glucose.

Where used herein the term "reaction accelerator" includes but is not limited to NaBr and KBr. The term "reaction initiator" where used herein is any compound which is effective in initiating the reaction in which $^{18}$F-FDG is converted into $^{18}$F-FGA, such as sodium hypochlorite (NaOCl) or calcium hypochlorite (Ca(ClO)$_2$). The term "reaction inhibitor" where used herein is any compound which is effective in inhibiting the reaction in which $^{18}$F-FDG is converted into $^{18}$F-FGA, such as ethanol. Where used herein, the term "reaction temperature" includes temperatures in a range of about 0° C. to about 25° C., including for example about 1° C. to about 10° C., and about 2° C. to about 5° C.

In certain non-limiting embodiments, the dosage of the active agent (e.g., $^{18}$F-FGA) administered to a subject, for example for PET imaging, contains an amount of the radionuclide active agent in a range of about 1 mCi to about about 50 mCi (or any amount inclusive in the range) such as about 5 mCi to about 30 mCi. However this amount is determined by the attending physician or diagnostician and may be either higher or lower than this range. The active agent will generally be introduced into the subject to be tested within about 3 hours after production of the active agent (e.g., $^{18}$F-FGA) to avoid loss of effectiveness due to decay of radioactivity. PET imaging will generally be performed from immediately after injection (0 hr) to about 4 hr after injection, depending on the clinical assessment desired to be performed. Standard imaging is generally performed within about 2 hr after injection.

The dosage(s) can be administered, for example but not by way of limitation, on a one-time basis, or administered at multiple times as needed, or continuously via a venous drip, depending on the desired effect, result, or condition of the subject treated. In one non-limiting example, the composition is provided in an IV infusion. Administration of the compounds used in the pharmaceutical composition or to practice the method of the present disclosure can be carried out in a variety of conventional ways, such as, but not limited to, orally, by inhalation, rectally, or by cutaneous, subcutaneous, intraperitoneal, vaginal, or intravenous injection. Oral formulations may be formulated such that the compounds pass through a portion of the digestive system before being released, for example it may not be released until reaching the small intestine, or the colon.

When a dosage comprising the active agent is administered orally, it may be in the form of a solid or liquid preparations such as capsules, pills, tablets, lozenges, melts, powders, suspensions, solutions, elixirs or emulsions. Solid unit dosage forms can be capsules of the ordinary gelatin type containing, for example, surfactants, lubricants, and inert fillers such as lactose, sucrose, and cornstarch, or the dosage forms can be sustained release preparations. The composition may contain a solid carrier, such as a gelatin or an adjuvant. The tablet, capsule, and powder may contain from about 0.05 to about 95% of the active substance compound by dry weight. When administered in liquid form, a liquid carrier such as water, petroleum, oils of animal or plant origin such as peanut oil, mineral oil, soybean oil, or sesame oil, or synthetic oils may be added. The liquid form of the composition may further contain physiological saline solution, dextrose or other saccharide solution, or glycols such as ethylene glycol, propylene glycol, or polyethylene glycol. When administered in liquid form, the composition particularly contains from about 0.005 to about 95% by weight of the active agent. For example, a dose of about 10 mg to about 1000 mg once or twice a day could be administered orally.

In another embodiment, the active agents of the present disclosure can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the compositions in an aqueous or non-aqueous pharmaceutically acceptable solvent which may also contain suspending agents, sweetening agents, flavoring agents, and preservative agents as are known in the art.

For parenteral administration, for example, the active agents may be dissolved in a physiologically acceptable pharmaceutical carrier, diluent, or vehicle and administered as either a solution or a suspension. Illustrative of suitable pharmaceutical carriers, diluents, or vehicles are water, saline, dextrose solutions, fructose solutions, ethanol, or oils of animal, vegetative, or synthetic origin. The pharmaceutical carrier, diluent, or vehicle may also contain preservatives and buffers as are known in the art.

When an effective amount of the active agent (imaging agent) is administered by intravenous, cutaneous, or subcutaneous injection, the compound is particularly in the form of a pyrogen-free, parenterally acceptable aqueous solution or suspension. The preparation of such parenterally acceptable solutions, having due regard to pH, isotonicity, stability, and the like, is well within the skill in the art. A particular composition for intravenous, cutaneous, or subcutaneous injection may contain, in addition to the active agent, an isotonic vehicle such as Sodium Chloride Injection, Ringer's Injection, Dextrose Injection, Dextrose and Sodium Chloride Injection, Lactated Ringer's Injection, or other vehicle as known in the art. The compositions of the present disclosure may also contain stabilizers, preservatives, buffers, antioxidants, or other additives known to those of skill in the art.

As noted, particular amounts and modes of administration can be determined by one skilled in the art. One skilled in the art of preparing formulations can readily select the proper form and mode of administration, depending upon the particular characteristics of the compositions selected, the condition to be assessed, and other relevant circumstances using formulation technology known in the art, described, for example, in *Remington: The Science and Practice of Pharmacy*, $21^{st}$ ed.

Additional pharmaceutical methods may be employed to control the duration of action of the compositions. Increased half-life and/or controlled release preparations may be achieved through the use of polymers to conjugate, complex with, and/or absorb the active substances described herein. The controlled delivery and/or increased half-life may be achieved by selecting appropriate macromolecules (for example but not by way of limitation, polysaccharides, polyesters, polyamino acids, homopolymers polyvinyl pyrrolidone, ethylenevinylacetate, methylcellulose, or carboxymethylcellulose, and acrylamides such as N-(2-hydroxypropyl) methacrylamide), and the appropriate concentration of macromolecules as well as the methods of incorporation, in order to control release. The compounds may also be ionically or covalently conjugated to the macromolecules described above.

Another possible method useful in controlling the duration of action of the compounds or compositions by controlled release preparations and half-life is incorporation of the compounds into particles of a polymeric material such as polyesters, polyamides, polyamino acids, hydrogels, poly (lactic acid), ethylene vinylacetate copolymers, copolymer micelles of, for example, polyethylene glycol (PEG) and poly(l-aspartamide).

Examples

The present disclosure will now be discussed in terms of several specific, non-limiting, examples and embodiments. The examples described below, which include particular embodiments, will serve to illustrate the practice of the present disclosure, it being understood that the particulars shown are by way of example and for purposes of illustrative discussion of particular embodiments and are presented in the cause of providing what is believed to be a useful and readily understood description of procedures as well as of the principles and conceptual aspects of the present disclosure.

Materials and Methods

Compounds from the following sources were used without further purification: D-Glucose (99.5%, Sigma-Aldrich, St. Louis, Mo., USA), 2-deoxy-D-glucose (98%, Alfa Aesar, Ward Hill, Mass., USA), 2-deoxy-2-fluoro-D-glucose (99%, Synquest Laboratories, Alachua, Fla., USA), 4-acetamido-2,2,6,6-tetramethylpiperidine 1-oxyl (TEMPO; 98%, Sigma-Aldrich), sodium bromide (Analytical grade, Mallinckrodt, Paris, Ky., USA), sodium hydroxide (Food Grade, Mallinckrodt), sodium bicarbonate (Laboratory grade, Sigma Aldrich), isoproterenol (ISO; Sigma-Aldrich), and sodium hypochlorite solution (14% available chlorine, Alfa Aesar). $^{18}$F-FDG was purchased from the University of Oklahoma-Nuclear Pharmacy.

High Performance Liquid Chromatography (HPLC)

HPLC was performed using a Beckman System Gold 128 Solvent Module (Beckman Coulter, Brea, Calif., USA) interfaced with a Rainin Dynamax UV-1 absorbance detector (Mettler Toledo, Columbus, Ohio, USA) set at 190 nm and a Bioscan B-FC-3300 (Bioscan, Washington D.C., USA) radioactivity detector. The reaction products were separated on a Phenomenex Rezex ROA-Organic Acid H+ (8%) column (300×7.8 mm) warmed to 70° C. Mobile phase consisted of 0.025 mM $H_2SO_4$ at a flow rate of 0.5 ml per minute.

Thin Layer Chromatography (TLC)

Whenever applicable, the reactions were monitored by TLC on 200 μm aluminum-backed Si 60 silica plates of 60 angstrom pore-size (EMD Millipore, Darmstadt, Germany). The developing solvent consisted of 7 parts n-butanol, 2 parts glacial acetic acid, and 3 parts water. The separated constituents were visualized by staining with iodine or using a mixture of 1 ml 37% HCl, 2 ml aniline, 10 ml 85% $H_3PO_3$, 2 g diphenylamine, and 100 ml ethyl acetate and developed at 200° C. on a hot plate. Under these conditions the Rf values of 4-acetamido-TEMPO, 2-deoxy-D-glucose, and 2-deoxy-D-glucaric acid were 0.62, 0.4, and 0.28, respectively. Radioactive reactions were analyzed on a Bioscan mini-scan 1000 (Bioscan, Washington D.C., USA).

Nuclear Magnetic Resonance (NMR)

$^1$H NMR spectra and $^{13}$C NMR spectra were recorded at 300 and 75 MHz on Mercury-VX 300 and Varian VNMRS-400 NMR Spectrometers and processed using Mnova (Santiago de Compostela, Spain). Spectra were referenced to the residual protonated solvents. Chemical shifts and coupling constants were reported in δ parts per million (ppm) and Hertz (Hz), respectively.

Oxidation of Glucose

We modified a previously reported TEMPO-based method to facilitate the synthesis of $^{18}$F-FGA at nanoscale. Approximately 30 mg of D-glucose (0.166 mmol), 2-deoxy-D-glucose (0.187 mmol), or 2-deoxy-2-fluoro-D-glucose (0.182 mmol) was added to a 5 ml round bottom flask containing 4-acetamido-TEMPO (8 mg, 0.038 mmol, 0.2 equivalents) and NaBr (80 mg, 0.77 mmol, 5 equivalents). Approximately 3 ml of 1M $NaHCO_3$ buffer (pH 11.6) was added, and the mixture was allowed to stir at room temperature for 5 min. The reaction mixture was cooled to 0-2° C. by incubating on ice for additional 3 min. NaOCl (14% solution, 0.75 ml, 1.69 mmol, 10 equivalents) was added in portions to the ice-cold reaction mixture over the course of 2 min. The reaction was monitored with KI strips for the presence of residual oxidizing agent. Upon complete consumption of the oxidizing agent, the reaction mixture was rapidly mixed with 40 ml of ice-cold ethanol, followed by centrifugation (5,000 rpm for 5 min) to collect the precipitate. The precipitate was washed with ice-cold ethanol and dried overnight at 100° C. The product was subjected to NMR and HPLC analyses. $^1$H NMR ($D_2O$, 300 MHz): δ 4.38 (br s, 2H, $H_1$, $H_4$), 4.26 (br s, 1H, $H_3$), 4.17 (br s, 1H, $H_2$). $^{13}$C NMR ($D_2O$, 75 MHz): δ 178.65, 178.60 ($C_6$, $C_1$), 73.85, 73.67, 73.57, 71.61 ($C_2$, $C_3$, $C_4$, $C_5$). $^1$H-NMR and $^{13}$C-NMRs matched with those cited in the literature.

Synthesis of $^{18}$F-FGA.

We adapted the procedures standardized for macroscale synthesis of oxidized glucose. Briefly, a mixture of 4-acetamido-TEMPO (0.8 mg), $NaHCO_3$ buffer (pH 11.6, 1 ml), NaBr (8 mg), and $^{18}$F-FDG (0.25-0.5 ml, ~20 mCi) was cooled to 0-2° C. in a 5 ml reaction vial. Approximately 20 μl of 14% NaOCl was added to the mixture to start the reaction. The reaction progress was monitored by sampling 5 μl of reaction mixture for radio-TLC. Upon completion of the reaction, the mixture was transferred into 10 ml ice-cold ethanol, followed by centrifugation (5000 rpm×5 min). The precipitate was washed once with ice-cold ethanol, 200 μl of 2 M HCl was added for neutralization, and the mixture was dissolved in 3 ml of water for injection. The clear solution was filtered sterile through 0.2 μm syringe filter. The final product was analyzed by radio-TLC as described above ($R_f$ of $^{18}$F-FDG=0.65 and $R_f$ of $^{18}$F-FGA=0.2).

In at least one embodiment, the present disclosure is directed to a method and kit for producing $^{18}$F-FGA, for use, for example, as a PET imaging agent. In one non-limiting embodiment, a reagent kit includes one or more reagent vials (e.g., 5-10 ml volume) containing an oxidizing agent such as TEMPO or a TEMPO derivative such as 4-acetamido-TEMPO, a reaction accelerator such as NaBr, and a buffering agent such as $NaHCO_3$ which are lyophilized, septa-sealed, and nitrogen-purged. At the time of synthesis, an amount of the radioactive precursor $^{18}$F-FDG (such as but not limited to, 5-30 mCi in about 0.5 ml) and a reaction initiator, such as sodium hypochlorite (NaOCl) or calcium hypochlorite ($Ca(ClO)_2$) are combined with the contents of the reagent vial containing the 4-acetamido-TEMPO, NaBr, and $NaHCO_3$ and the reaction is allowed to proceed at 2-4° C. (e.g., in an ice bath). NaOCl is provided as a solution (e.g., a 14% solution). When $Ca(ClO)_2$ is used as the reaction initiator instead of NaOCl, it can be provided for example as a solid-phase alternative, and optionally can be contained in the reagent vial. The cold temperature can be maintained, for example, by using ice-bath, aluminum block, pre-cooling $^{18}$F-FDG, or a combination of such steps. After a duration of time, e.g., 3-6 min, the reaction is stopped, for example by adding 0.1 ml of ethanol. Alternatively, the ethanol addition step can be eliminated if the standardized conditions do not result in over-oxidation of $^{18}$F-FDG, for example by optimizing the concentration of the reaction initiator (NaOCl or $Ca(ClO)_2$). Generally 100% of the $^{18}$F-FDG is converted into $^{18}$F-FGA with no side reactions, eliminating the need of purification. However, if desired or otherwise necessary, the $^{18}$F-FGA reaction product can be separated from precursor $^{18}$F-FDG, for example by using an anion exchange cartridge or HPLC. Radiochemical purity of the product will be assessed with radioactive-TLC. For example, in a non-limiting embodiment, in a system of 95% acetonitrile/5% acetic acid, the flow of $^{18}$F-FGA is slower as compared to that of $^{18}$F-FDG. In another non-limiting embodiment, a system of 90% acetonitrile/10% water can be used. The final $^{18}$F-FGA product is adjusted for pH (e.g., 6.5-7.5 pH) and osmolality (e.g., 300±15 mOsmol), filtered sterile (0.2 μm), and can be characterized by radio-HPLC. The reagent kit will generally further include instructions for combining the contents of the kit with $^{18}$F-FDG to produce the $^{18}$F-FGA. In one non-limiting embodiment, the reagent kit includes a first reactant container, such as a vial, containing (1) an oxidizing agent such as TEMPO or a TEMPO-derivative, (2) a reaction accelerator such as NaBr or KBr, and (3) a buffering agent such as $NaHCO_3$, and a second container, such as a vial, containing a reaction initiator NaOCl. Optionally the kit includes a container of a reaction inhibitor such as ethanol.

In another non-limiting embodiment, the reagent kit includes a first reactant container, such as a vial, containing (1) an oxidizing agent such as TEMPO or a TEMPO-derivative, (2) a reaction accelerator such as NaBr or KBr, (3) a buffering agent such as $NaHCO_3$, and (4) a reaction initiator $Ca(ClO)_2$. Optionally the kit includes a container of a reaction inhibitor such as ethanol. The kit may optionally include quality control components such as thin layer chromatography strips and/or solvents.

The following non-limiting scenario can be envisioned for use of the kit in producing $^{18}F$-FGA and as a method of use of the $^{18}F$-FGA product, for example for use in a PET imaging procedure. In one embodiment, a physician customer desires to perform $^{18}F$-FGA imaging for detecting necrosis in MI or stroke (or other condition in which necrosis is desired to be detected, such as in breast, prostate, lung, or colon tissue). The physician (or other user such as a technician) communicates with a nuclear pharmacy and requests a quantity of $^{18}F$-FGA. The nuclear pharmacy produces the $^{18}F$-FGA according to methods described herein, such as by using the reagent kit containing the 4-acetamido-TEMPO, NaBr, and $NaHCO_3$ (and optionally $Ca(ClO)_2$), or by manually combining separate reactants as described hereinabove, for example. The product $^{18}F$-FGA is delivered to the physician's office or imaging facility for the clinical study.

Biodistribution Studies in Mice

All animal work described herein was performed according to the NIH Animal Use and Care Guidelines and was approved by the institutional IACUC. Nine male and three female CD1 mice (20-36 g) were obtained from Harlan Laboratories (Indianapolis, Ind.), and housed in a controlled environment with 12 h day/night cycle. The mice were allowed to acclimatize for at least 1 week before inclusion in the study. On the day of imaging, the animals were anesthetized with 2-3% isoflurane in oxygen stream. Approximately 100 µCi of $^{18}F$-FGA was injected intravenously in the tail vein. The animals were placed in a cage with absorbent padding until biodistribution. Briefly, the mice were euthanized after 1 or 3 hours post injection by an over-dose of isoflurane (4%) followed by cervical dislocation. Various organs were excised, washed with saline, weighed, and appropriate tissue samples were counted in an automated gamma counter (Packard Cobra II Auto Gamma, Perkin Elmer, Boston, Mass.). Total blood volume, bone, and muscle mass were estimated as 5.7%, 10% and 40% of body weight, respectively. A diluted sample of injected $^{18}F$-FGA served as a standard for comparison.

Circulation Kinetics

Five male CD-1 mice were injected with 100 µCi of $^{18}F$-FGA intravenously via the tail vein. At 0, 30, 60, 90, 120, and 180 minutes post injection, 25-50 µl of blood was sampled from the retro-orbital sinus. Blood was weighed and counted in an automated gamma counter (Packard Cobra II Auto Gamma, Perkin Elmer, Boston, Mass.). One mouse was excluded from the study based on macroscopic observations about the abnormal kidney morphology upon necropsy.

Rat Model of ISO-Induced Myocardial Damage

Male Sprague Dawley rats (250-300 g) were purchased from Harlan (Indianapolis, Ind., USA), housed in regular light/dark cycles and allowed to acclimatize for at least 5 days prior to the experiments. Myocardial injury was induced by administering a sterile aqueous solution of ISO at a dose rate of 150 mg/kg bodyweight. The drug was intraperitoneally injected on two consecutive days.

Electrocardiography (ECG)

Lead 1 ECG of isoflurane-anesthetized rats was recorded by placing negative electrode on the right front paw, positive electrode on the left front paw, and ground lead on to the left hind paw. The electrodes were secured to the lead (CB Sciences C-ISO-255), bioamplifier (ETH-225), and analog to digital converter (iWorx 118) and the signal was recorded using Labscribe 2.0 software (iWorx, Dover, N.H.). Before analysis of raw data, the signal was filtered to eliminate 60 Hz mains frequency.

Imaging

The rats were subjected to three imaging sessions post-injury: $^{18}F$-FGA imaging on the third day, followed by $^{99m}Tc$-Sestamibi imaging and $^{18}F$-FDG imaging on the fourth day. In addition to the post-injury imaging, baseline images were also acquired before inducing ISO-injury. The doses of $^{18}F$-FGA, $^{99m}Tc$-Sestamibi, and $^{18}F$-FDG were 1 mCi (0.5-1 ml), 2.5 mCi (0.5-1 ml), and 0.1 mCi (0.2-0.4 ml), respectively. All injections were given intravenously in the tail vein of anesthetized (2% isoflurane-oxygen mixture) rats and imaging was performed at indicated times after the injections. Through the imaging period, anesthesia was maintained with a 2% isoflurane-oxygen mixture. For PET, the rats were positioned supine in a gantry of a PET-CT dual modality machine (Gamma Medica Ideas, Northridge, Calif.). A fly-mode CT of thoracic region was acquired before a 20 min list mode PET data acquisition. SPECT imaging was performed on a NanoSPECT machine (Trifoil Imaging, Chatsworth, Calif.) by helical SPECT acquisition of the thoracic region in 24 frames of 60 seconds each. After imaging, the rats were allowed to wake up and kept in their cage until the time of euthanasia.

The acquired PET images was reconstructed by filtered back projection algorithm and fused with the CT to generate a composite PET-CT image. SPECT acquisitions were reconstructed with HiSPECT reconstruction algorithm provided with the system.

Standard uptake value (SUV) was calculated by defining a three-dimensional region of interest (ROI) around the heart using the CT image. Background was determined by placing a spherical ROI at the same level as the $4^{th}$ sternebrae in the XY plane in the posterior medial area of the left lung. Mean counts per voxel for the heart were normalized to mean background counts per voxel.

Cardiac Troponin I Assay

Blood samples were collected before euthanasia and plasma was separated by centrifugation (5,000 rpm for 5 min). We determined the levels of cardiac TnI (cTnI) in plasma by using a rat-specific enzyme-linked immunoassay kit obtained from Life Diagnostics (West Chester, Pa.). The plasma samples were diluted 1:2 with PBS before estimation.

Corticosterone Enzyme-Linked Immunosorbent Assay (ELISA)

We measured the concentration of stress hormone corticosterone in undiluted plasma by using an ELISA kit from Cayman Chemicals (Ann Arbor, Mich.). Corticosterone is the only glucocorticoid present in rats.

2,3,5-Triphenyltetrazolium Chloride (TTC) Staining

After the final session of imaging and blood sample collection, the rats were euthanized and their hearts were immediately collected and frozen at −20° C. for 2 h. The hearts were sectioned into 2 mm slices and placed in 1% solution of TTC in PBS at 37° C. with intermittent shaking. After 30 min of staining, the TTC was removed and replaced with 10% buffered fomialin overnight.

Data Analysis

For statistical comparisons we employed GraphPad Prism 6 Software (GraphPad, La Jolla, Calif.). Two group comparisons were performed using a Student's T Test, comparisons between 3 or more groups were done using one way ANOVA. Pharmacokinetic parameters were calculated from the semi-log plot of time-activity curves using method of residuals.

Middle Cerebral Artery Occlusion (MCAO) Mouse Model

Fasted mice are anesthetized with 1.5% isoflurane in a stream of $O_2:N_2$ mixture (30:70, 1 L/min) and blanketed in a thermostatic blanket at 37° C. The left occipital and superior thyroid arteries, branches of the external carotid artery (ECA), the pterygopalatine artery, branch of internal carotid artery (ICA) are electro-coagulated and cut. The common carotid artery is occluded by a micro-clip. The left ECA is ligated, coagulated, and cut distal to the cranial thyroid artery. A 15 mm monofilament nylon suture (6-0, dia of heat-rounded tip=0.2-0.3 mm) is inserted into the ECA and gently advanced through the ICA until its tip has occluded the origin of the MCA. Correct placement of the suture is indicated by a sudden drop of the local cortical blood flow in the left MCA territory to 10-20% of basal flow. CBF is monitored by non-invasive laser Doppler flowmetry (Moor Instruments). A sustained reduction of >80% is indicative of successful MCAO. The monofilament is secured in place with a ligature and the skin incision is closed. The monofilament suture is left in place for permanent MCAO, but for transient MCAO, the occluding suture is removed after 1 h by anesthetizing the mouse and re-opening the wound.

Results

Synthesis of Glucaric Acid from Glucose

Figure 2:
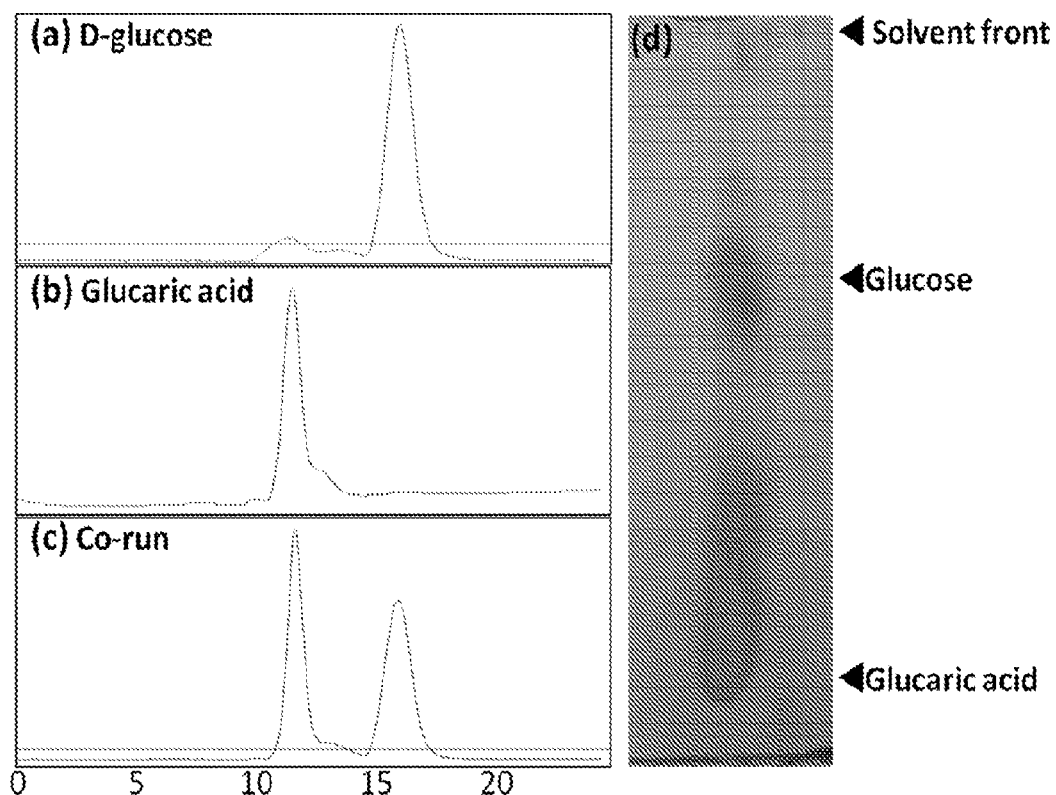
FIG. 2 shows high pressure liquid chromatography (HPLC) results of (a) d-glucose, (b) d-glucaric acid, and (c) separation of a mixture of d-glucose and d-glucaric acid, and (d) a thin-layer chromatogram (TLC) showing separation of a mixture of d-glucose and d-glucaric acid.

A TEMPO/NaBr/NaOCl system was used to oxidize glucose to glucaric acid (see Scheme 1 in FIG. 1). The reaction progress was monitored by the consumption of oxidizing agent which was read with KI strips. The oxidation reaction was generally completed within 20 min of addition of NaOCl to the reaction mixture. An increase in the concentration of oxidizing agents led to an increase in reaction rate, but it also resulted in an increased tendency to over-oxidize glucose into undesired cleaved products. Glucose and glucaric acid were effectively separated by HPLC on an ROA column (FIG. 2a-c) with retention times of 16 min and 12 min, respectively. In butanol:water:acetic acid (7:3:2 v/v) TLC system, glucose and glucaric acid exhibited $R_f$ values of 0.62 and 0.28, respectively (FIG. 2d). The ethanol-precipitated product of reaction performed under optimal conditions was characterized by $^1$H NMR which showed exclusively glucaric acid. Any side product, TEMPO or residual glucose remained in the supernatant. Gravimetric analysis of the precipitate showed that the excess sodium bicarbonate also precipitated with the glucaric acid which could be neutralized by addition of equivalent concentration of HCl.

Synthesis of $^{18}$F-FGA from $^{18}$F-FDG

Figure 3:
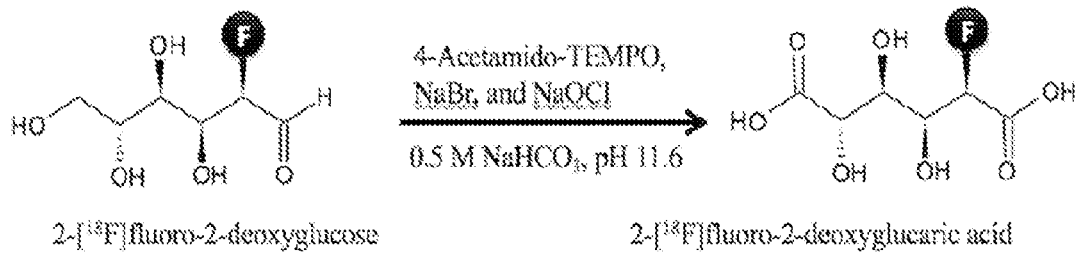
FIG. 3 shows an oxidation reaction to produce [$^{18}$F] fluoroglucaric acid ($^{18}$F-FGA) from commercially available 2-deoxy-2-[$^{18}$F]fluoro-D-glucose ($^{18}$F-FDG) using a TEMPO/NaBr/NaOCl system.
Figure 4:
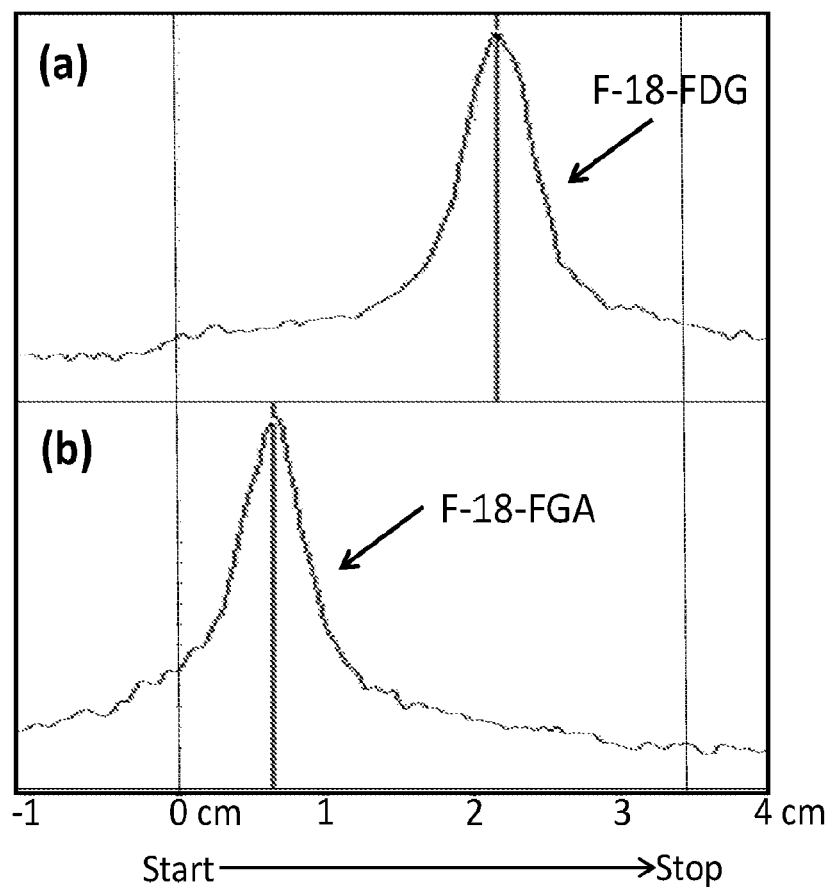
FIG. 4 shows radio-TLC chromatograms of (a) $^{18}$F-FDG (F-18-FDG), and (b) $^{18}$F-FGA (F-18-FGA).

We adapted the synthetic process of Scheme 1 to produce $^{18}$F-FGA from commercially available $^{18}$F-FDG (see Scheme 2, FIG. 3). Use of strong bicarbonate buffer allowed the reaction to proceed without the need to monitor and adjust pH. The oxidizing reagents were proportionately reduced, and the reaction was performed inside a lead-shielded box. The reaction was monitored for completeness by radio-TLC (FIG. 4a-b). As shown in a time course of reaction monitored by radio-HPLC (FIG. 5a-d), the reaction proceeded quite rapidly, and the $^{18}$F-FDG was entirely consumed within about 3 min of the addition of bleach (NaOCl). Extending the reaction up to 6 min did not appear to result in production of undesirable side products. The last chromatogram in this series shows the profile of the $^{18}$F-FGA after ethanol precipitation, centrifugation, washing, and re-dissolution of pellet in water for injection (FIG. 5e). We usually obtained more than non-decay-corrected 50% yield, and the synthesis, purification, and TLC-quality control were accomplished routinely within 1 h.

Biodistribution of $^{18}$F-FGA in Mice

Results of a whole body distribution analysis of $^{18}$F-FGA in various organs of normal mice 1 and 3 h after injection are shown in Table 1. Normal healthy mice were injected with $^{18}$F-FGA (0.1 mCi) via the tail vein and the mice were euthanized at 1 h and 3 h post injection. The majority of injected radioactivity was found to be excreted via the renal system. All other organs accumulated less than 0.5% of the injected dose/g tissue. The concentration of $^{18}$F-FGA in circulation was also negligible. These results suggested that $^{18}$F-FGA is rapidly cleared from the body and does not accumulate in liver, lung, or bone, which are the tissues with potential to obfuscate myocardial imaging.

TABLE 1

Biodistribution of $^{18}$F-FGA in mice.

| Tissue | 1 hour (n = 8) | 3 hour (n = 4) |
| --- | --- | --- |
| Brain | 0.039 ± 0.027 | 0.014 ± 0.007 |
| Muscle | 0.049 ± 0.025 | 0.03 ± 0.018 |
| Heart | 0.056 ± 0.027 | 0.018 ± 0.01* |
| Spleen | 0.074 ± 0.036 | 0.033 ± 0.015 |
| Blood | 0.145 ± 0.095 | 0.051 ± 0.025 |
| Lung | 0.192 ± 0.087 | 0.104 ± 0.073 |
| Liver | 0.417 ± 0.128 | 0.087 ± 0.027*** |
| Bone | 0.321 ± 0.128 | 0.727 ± 0.773 |
| Kidney | 4.226 ± 3.281 | 0.698 ± 0.378 |

Figure 6:
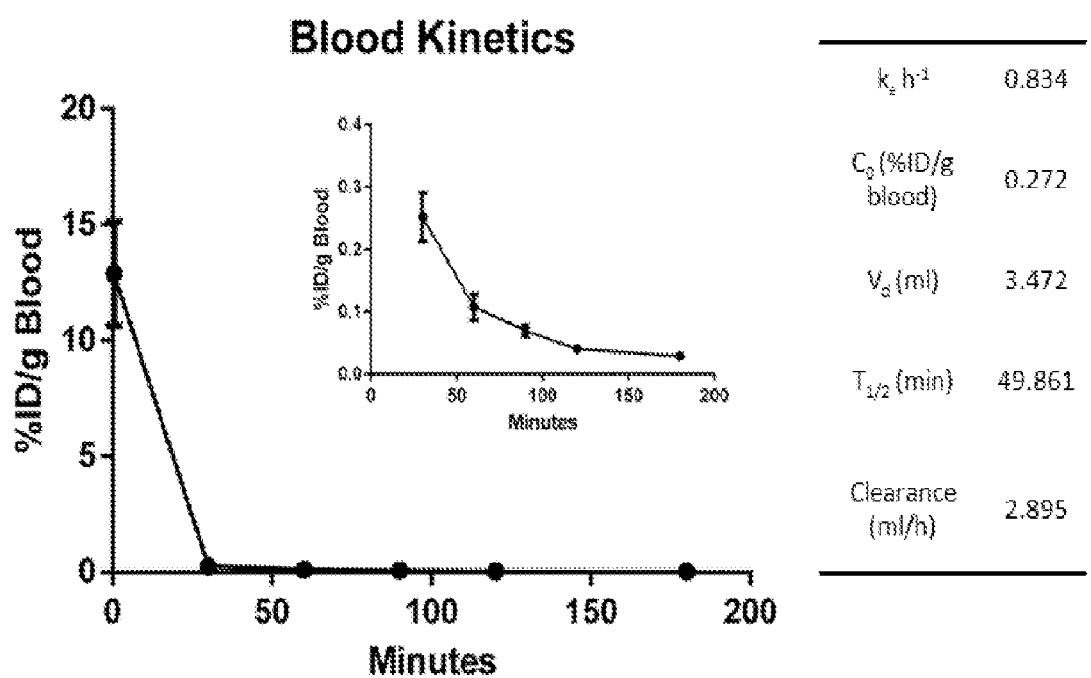
FIG. 6 shows circulation kinetics of $^{18}$F-FGA. Data is presented as the means and SEM (n=4). Pharmacokinetic parameters were derived from the 30-180 minute time points.

Values are decay-corrected % ID/g tissue presented as mean ± SD. Comparisons between 1 and 3 h time-points were done with a student's T Test.
*$P < 0.05$,
***$P < 0.001$ Circulation Kinetics of $^{18}$F-FGA in Mice Circulation kinetics of $^{18}$F-FGA was studied over the course of 3 h. As shown in FIG. 6 (left panel), by 30 min, more than 99% of the injected dose was removed from circulation. From the elimination phase of the time-activity relationship we calculated the half-life to be approximately 35 minutes and the elimination rate constant to be 0.83 h$^{-1}$. Pharmacokinetic parameters were calculated from the 30-180 minute time points and are presented in tabular form (FIG. 6, right panel).

ISO-Induced Myocardial Injury in Rats

Figure 7:
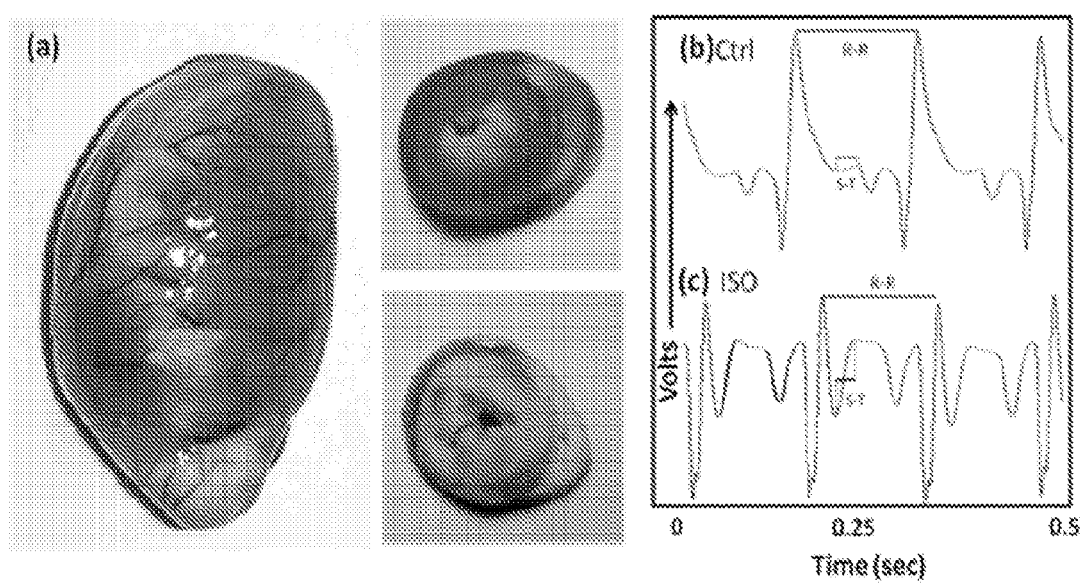
FIG. 7 shows macroscopic histology images of heart in ISO-injected rat. The left panel of (a) shows an entire heart excised from ISO-treated rat. About 30 min before euthanasia, the rat was injected with 1% Evan's blue dye (2 ml/kg). TTC-stained slices (right panel of (a)) were fixed in formalin. The damaged tissue is indicated by unstained (pale) regions, whereas the normal tissue is shown as darker-stained regions. Lead I ECG recordings in these animals as a function of ISO-treatment are shown in FIG. 5(b-c).
Figure 8:
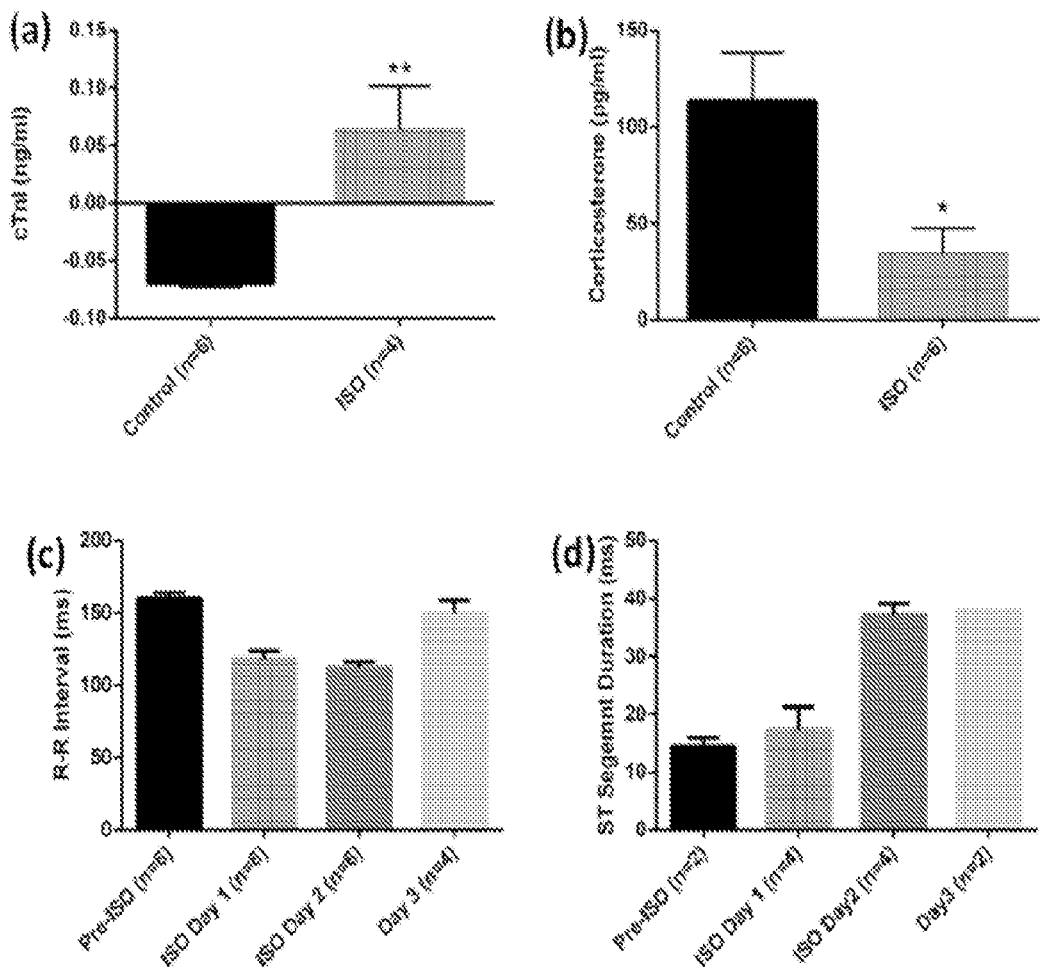
FIG. 8 shows results of isoproterenol (ISO)-induced myopathy: (a) Cardiac troponin levels and (b) corticosterone levels before and after treatment with ISO. Comparisons were done with a two tailed students T-test. (c) ECG readings show a decrease in RR interval on the days of ISO treatment with a return to normal after ISO treatment (d) ST prolongation indicates delayed ventricular repolarization as a result of ISO administration. Comparisons with (c) and (d) were done with a one-way ANOVA. *p<0.05, **p<0.01.

As shown in FIG. 7a, after two consecutive days of ISO injection, a representative whole heart perfused with Evans blue and sections of TTC-stained heart slices showed areas of generalized and extensive necrosis (white regions). Lead I ECG recordings in these animals as a function of ISO-treatment are shown in FIG. 7b-c. ECG changes occurred in all ISO treated animals, but because ISO treatment creates non-specific areas of necrosis the changes were not consistent in severity or defect across rats. However, on the same day of ISO treatment the R-R interval was significantly decreased indicating an increased heart rate (FIG. 8c). Over the course of ISO treatment the ST duration also increased (FIG. 8d). This indicated that ventricular repolarization was delayed, which can be caused by prolonged action potentials in the purkinje fibers which is known to occur as a result of administration of cardiotoxic agents.

Cardiac troponin was undetectable in control/baseline plasma (n=6), but was found to be 63 pg/ml (n=4) in ISO-treated rat plasma (FIG. 8a). While the troponin levels were significantly increased, they are not as high as would be expected because the post-ISO plasma samples were obtained 24-48 hours after ISO administration. By this time, much of the circulating troponin is expected to be cleared from the blood. The plasma concentrations of corticosterone are shown FIG. 8b. Plasma levels of corticosterone in ISO-treated rats (34.1 ng/ml, n=6) were significantly reduced as compared to the baseline levels (113.5 ng/ml, n=5) as was expected with ISO administration.

Figure 9:
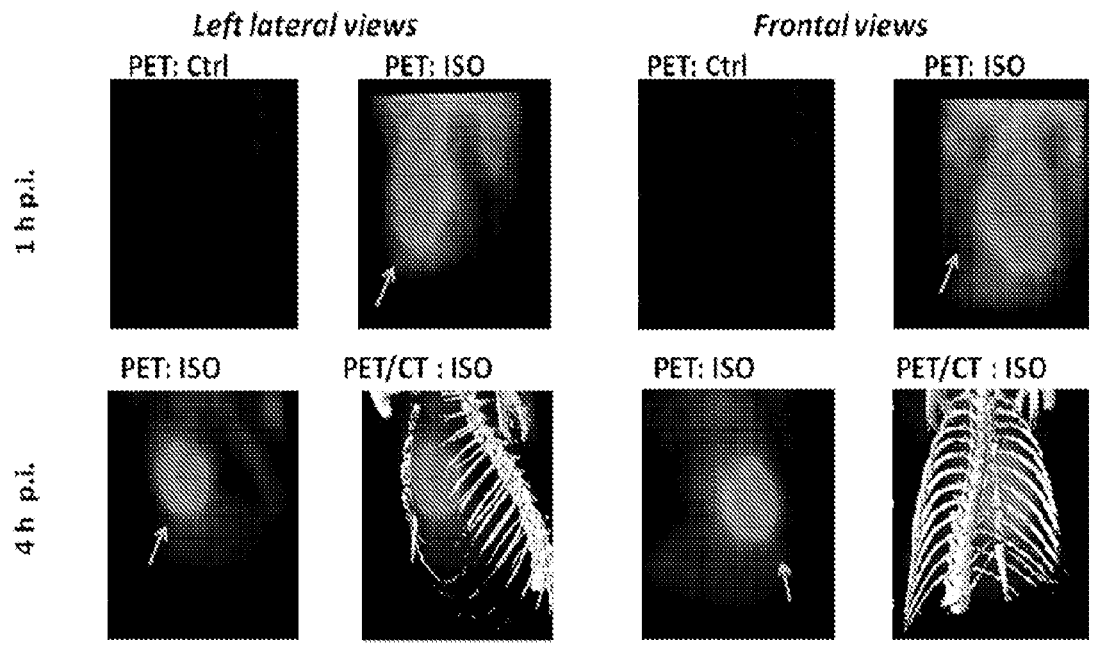
FIG. 9 shows representative PET images of an ISO-treated rat injected with approximately 1 mCi of $^{18}$F-FGA. The rat was imaged at 1 h and 4 h post-injection. Fused PET/CT images, frontal and left lateral, are shown for orientation of the viewer. Heart is indicated by arrows.
Figure 10:
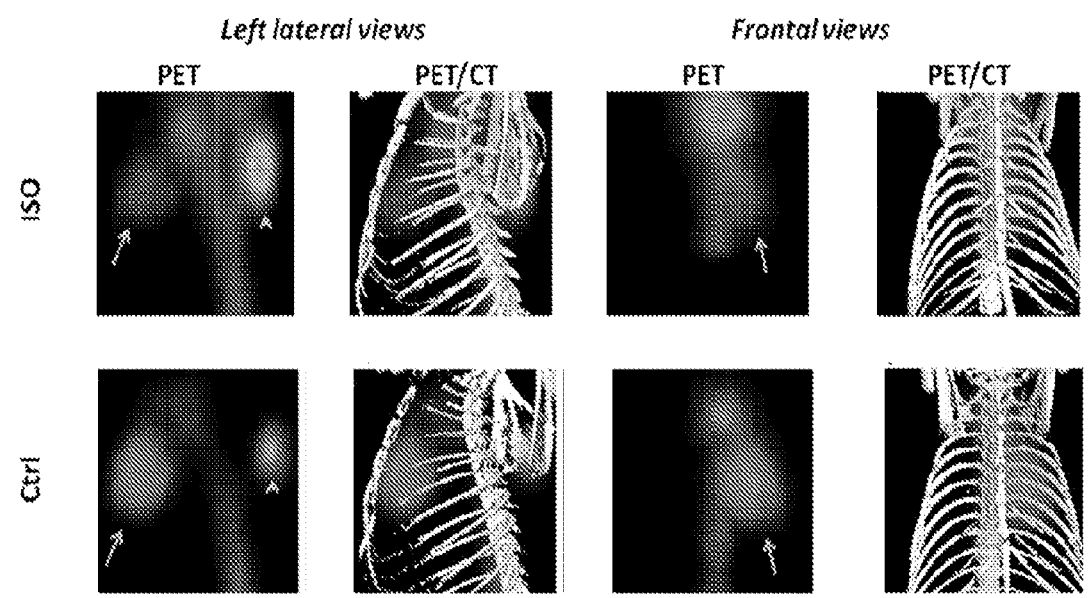
FIG. 10 shows representative PET images of control and ISO-treated rats injected with approximately 0.1 mCi of $^{18}$F-FDG. The rat was imaged at 1 h post-injection. Fused PET/CT images, frontal and left lateral, are shown for orientation of the viewer. Heart is shown by arrows, whereas brown fat is indicated by arrowheads.
Figure 11:
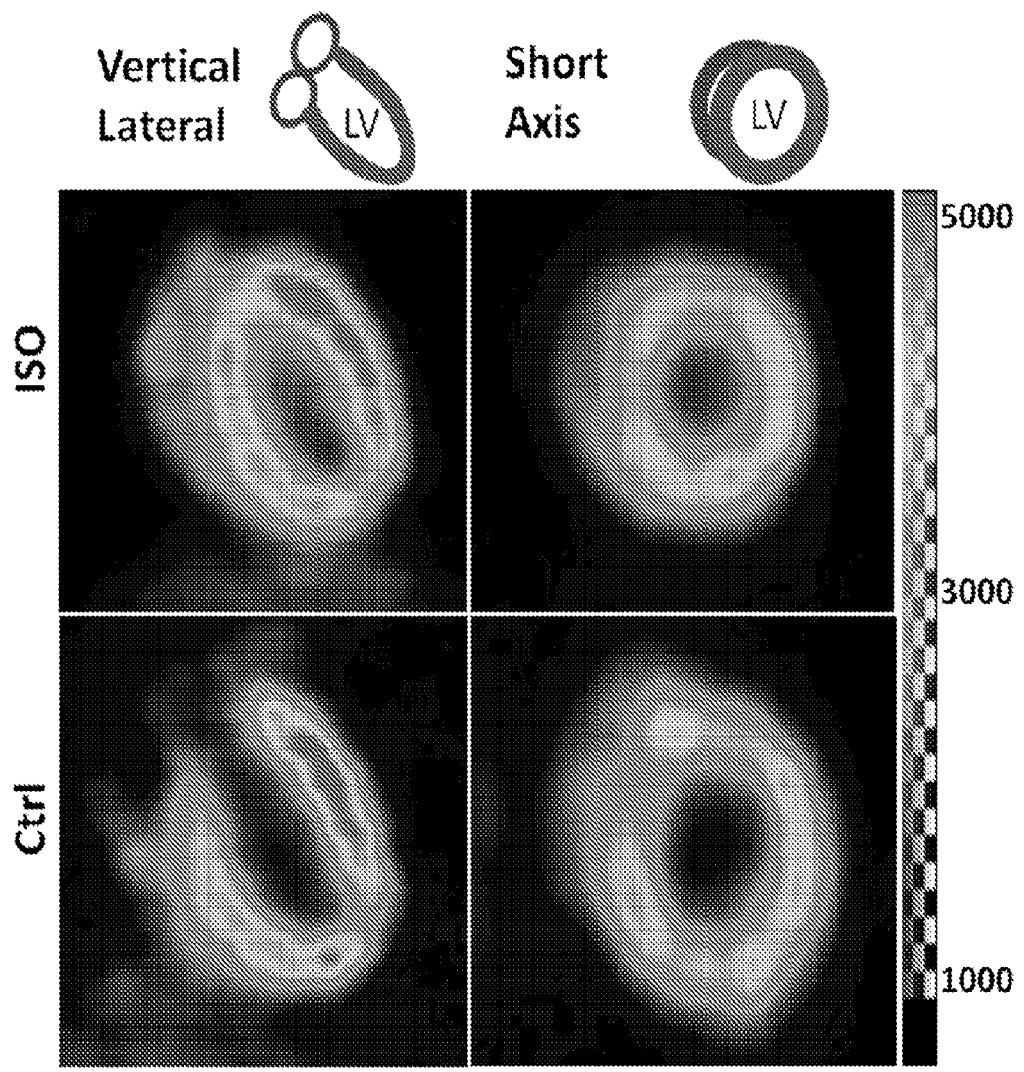
FIG. 11 shows a representative scan from perfusion imaging using $^{99m}$Tc-Sestamibi (a.k.a., Tc-99m-MIBI). Control and ISO-treated rats were injected with approximately 2.5 mCi of Tc-99m-MIBI and imaged after 1 h.

Accumulation of $^{18}$F-FGA, $^{99m}$Tc-Sestamibi, and $^{18}$F-FDG in ISO-Induced Myocardial Injury Rats were imaged with $^{18}$F-FGA before treating with ISO and after two consecutive days of ISO treatment. Results are shown in FIG. 9. We found negligible uptake in normal (baseline) myocardial tissue, but the 1 h images of ISO-treated rats the cardiac tissue accumulated large amounts of injected $^{18}$F-FGA. The contrast between $^{18}$F-FGA accumulation in myocardial tissue and non-target tissues became very pronounced when the imaging was repeated at 4 h post-injection. The rats were also imaged by two clinically utilized imaging agents, namely $^{99m}$Tc-Sestamibi and $^{18}$F-FDG, on the day immediately after the day of $^{18}$F-FGA imaging in control and ISO-treated rats. FIG. 10 shows PET images 1 h after $^{18}$F-FDG injection and FIG. 11 shows SPECT images 1 h after $^{99m}$Tc-Sestamibi administration. $^{99m}$Tc-Sestamibi-SPECT was unable to delineate ISO-induced myocardial pathology (FIG. 11). $^{18}$F-FDG-PET, on the other hand, showed reduced myocardial accumulation of $^{18}$F-FDG in ISO-treated rats. Based on ROI-based analysis of images, the reduction in $^{18}$F-FDG uptake was approximately 48% between control and ISO treated rats.

$^{18}$F-FGA Does not Accumulate in Normal Brain and is Rapidly Cleared from the Body of Normal Mice.

We injected 0.1 mCi (50 µl) of $^{18}$F-FGA in normal healthy mice (n=8), and collected organs for counting at 1 h post-injection. The accumulation in the brain was less than about 0.1% and in all major organs was below 0.5% of the injected dose and it cleared via renal system. It is noteworthy that clinically used brain perfusion agent $^{99m}$Tc-HMPAO (Ceretec) and $^{18}$F-FDG significantly accumulate in brain which introduces significant problems in image interpretation. Rapid clearance and absence of accumulation in healthy cerebral tissue indicated effectiveness of $^{18}$F-FGA for clear infarct imaging.

$^{18}$F-FGA Localizes in Infarct Region in a Mouse with Permanent MCAO.

Figure 12:
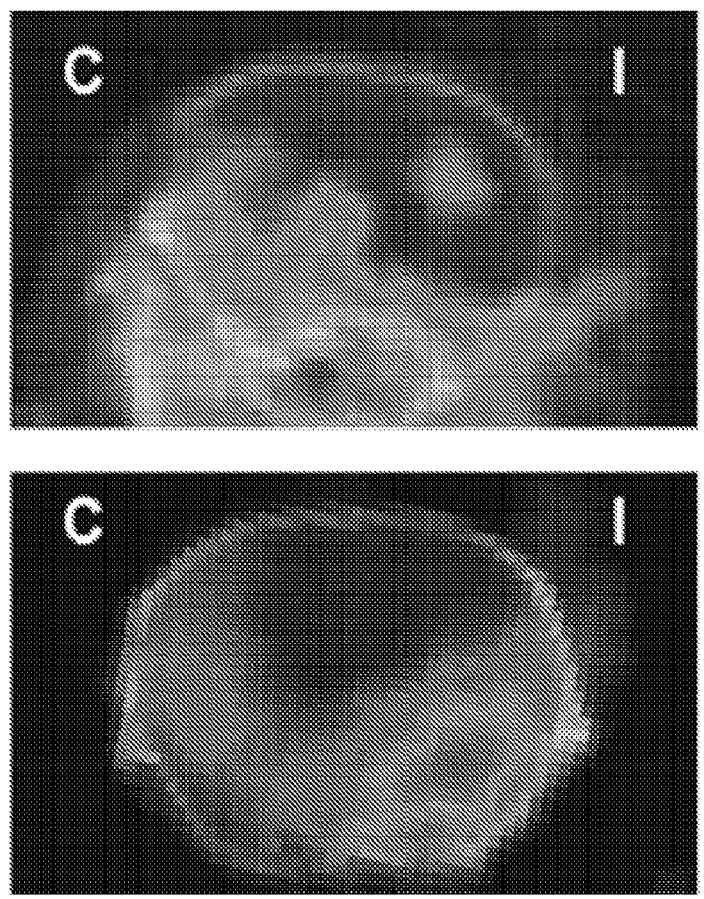
FIG. 12 shows PET images which show ipsilateral (I) vs contralateral (C) accumulation of $^{18}$F-FGA in a mouse MCAO model. Top image is after 2 hr of MCAO and bottom image is after 24 hr of MCAO.

$^{18}$F-FGA was found, in the present work, to accumulate in the brain of a mouse model of brain stroke created by middle cerebral artery occlusion (MCAO). To test $^{18}$F-FGA for imaging infarct in brain, we employed a mouse model of permanent MCAO. PET was performed after 2 h of MCAO surgery. Approximately 1 mCi of $^{18}$F-FGA was injected (i.v.) and a 20 min image was acquired after 1 h of injection. The ipsilateral side showed a central area of $^{18}$F-FGA accumulation, but the perfusion around this core region was significantly reduced; the contralateral side showed exact opposite scenario (FIG. 12, top). We also performed 1 day post-MCAO imaging of brain excised after 2 h of $^{18}$F-FGA injection. This image of excised brain clearly showed higher accumulation in the ipsilateral side than the contralateral side (FIG. 12, bottom).

Figure 13:
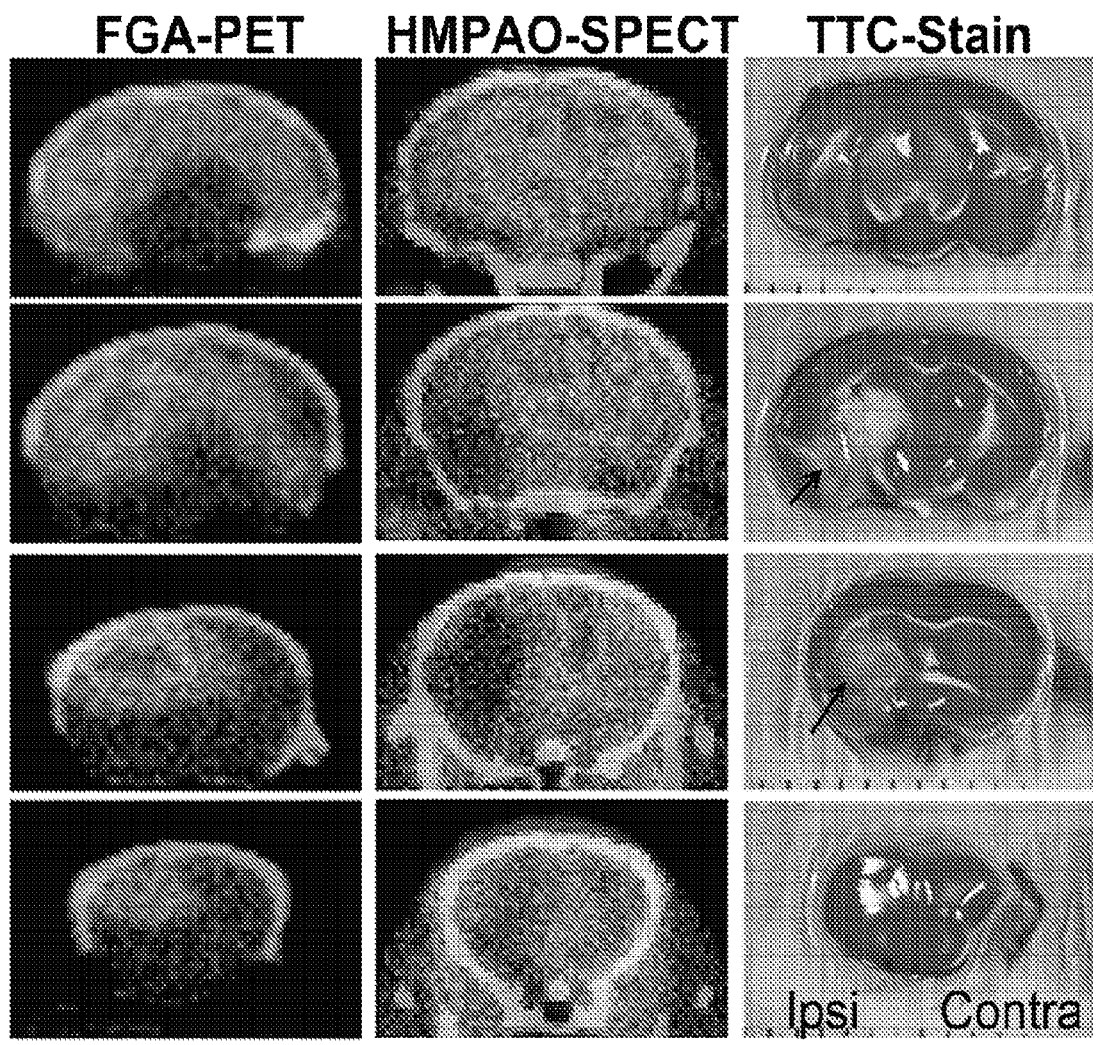
FIG. 13 shows evidence that $^{18}$F-FGA localizes in necroses caused by brain stroke $^{18}$F-FGA accumulates in stroke regions of ipsilateral cerebral hemisphere in a mouse model of middle cerebral artery occlusion (left-hand column). Corresponding perfusion images of HMPAO/SPECT show deficient uptake in stroke regions, but normal uptake in contralateral cerebral hemisphere (center column). TTC-stained slices of brain at necropsy (right-hand column) show stroke regions indicated by arrows.

Further evidence that $^{18}$F-FGA localizes in necroses caused by brain stroke is shown in FIG. 13. $^{18}$F-FGA accumulates in stroke regions of ipsilateral cerebral hemisphere in a mouse model of middle cerebral artery occlusion (left-hand column). Corresponding perfusion images of HMPAO/SPECT show deficient uptake in stroke regions, but normal uptake in contralateral cerebral hemisphere (center column). TTC-stained slices of brain at necropsy (right-hand column) show stroke regions indicated by arrows.

An example of a process and set of kit instructions for making $^{18}$F-FGA from $^{18}$F-FDG, and assessing product quality is shown below. It is not intended that the embodiments of the present disclosure for the making, use, and analysis of an $^{18}$F-FGA product be limited to the processes and instructions shown in the below example.

I. Kit Instructions for Synthesis of F-18-FGA ($^{18}$F-FGA) from F-18-FDG ($^{18}$F-FDG)

II. Glucaric acid is a derivative of glucose in which both terminal ends have been oxidized into carboxylic acids. It is also produced by the body in the natural course of glucose metabolism and is considered GRAS (generally recognized as safe) by the US FDA. Glucaric acid has a tendency to accumulate in the areas of acute necrosis, purportedly because of its affinity to the exposed positively-charged histone proteins in dying tissue. This kit enables the user to convert commercially available F-18-FDG ($^{18}$F-FDG) into a sterile dose of F-18-FGA ($^{18}$F-FGA). F-18-FDG is widely used by positron emission tomography (PET) centers for imaging of cancer, brain, and heart diseases.

III. Materials supplied in kit
  1. Component A: Lyophilized vial containing 4-Acet-amido-TEMPO (0.8 mg), NaBr (8 mg), and NaHCO$_3$ (24 mg)
  2. Component B: Sterile NaOCl (14% available chlorine in water) in a ready to use syringe
  3. Component C: Sterile HCl (0.2 N, 1.5 mL) in a ready to use syringe
  4. A glass bottle containing TLC solvent (90% Acetonitrile/10% water)
  5. TLC Strips (Silica Gel 60 on aluminum backing)
  6. pH paper strip
  7. Syringe Filter (0.2 µM MCE)

IV. Materials supplied by user:
F-18-FDG (1-50 mCi in approximately 0.2-2 mL) for injection V. Storage:
Kit should be stored at 4° C. until use.

VI. Method of making F-18-FGA product:
Inject F-18-FDG into the Component A vial followed immediately by injection of Component B into the Component A vial. Gently mix and wait for 5 min before injecting the contents of Component C into the Component A vial. Mix by swirling and withdraw the contents of the Component A vial into a sterile syringe. Optionally, the contents can be filtered through the supplied 0.2 µM syringe filter.

Figure 14:
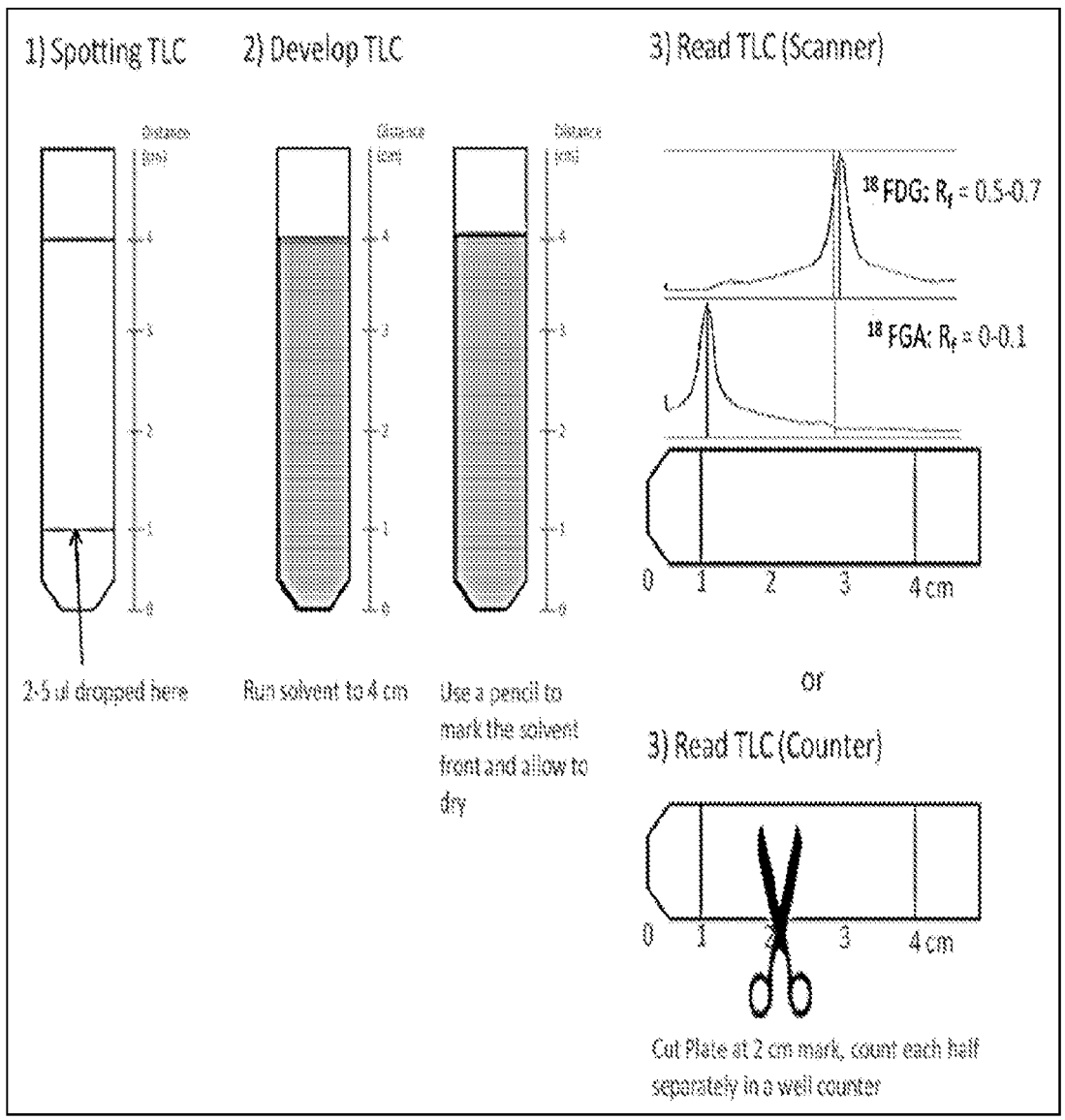
FIG. 14 shows a non-limiting example of a thin layer chromatography (TLC) protocol for quality control in a method of $^{18}$F-FGA production from $^{18}$F-FDG.

VII. Quality assessment of F-18-FGA product:
Radiochemical purity: Spot a drop of precursor F-18-FDG and product F-18-FGA on two separate TLC strips (see figure entitled TLC Protocol for Quality Control of F-18-FGA Production [FIG. 14]). Allow the spot to dry for 1-2 min. Develop TLC strips in the supplied up to 40 mm. Mark the solvent front with a pencil. Cut the TLC strips at 20 mm from the origin and measure the radioactive counts in the top and bottom pieces in a well counter to calculate % conversion. The % conversion value should exceed 95%. Alternatively, a radio-TLC reader could be used to read the strips without cutting.

% Conversion=100×Counts in bottom piece/(Counts in bottom piece+Counts in top piece).

pH of the injection (6.5-7.5): Place a small drop (25-50 μL) of preparation on a pH paper strip to confirm pH.

The instructions can be a package insert provided with the kit, or can be accessible virtually by a user of the kit via a uniform resource locator (URL) or web address provided with the kit.

Discussion

Acute myocardial infarction (MI) is the most severe form of cardiac dysfunction which accounts for millions of deaths worldwide. More than 1.1 million US hospital admissions in 2010 were attributed to MI. Rapid diagnosis is important for favorable prognosis in these patients. Primary diagnosis of MI can be based on changes in classic electrocardiography (ECG), but ECG can be inconclusive in many instances. Since myocyte necrosis is the end result of all ischemic events, elevation of cardiac troponin in peripheral blood has emerged as a commonly used biomarker of necrosis. However, there are many instances when troponin levels may not accurately reflect cardiac status. High-sensitivity cardiac troponin has been reported stable in patients with clinical diagnosis of non-ST-segment elevation MI. Secondly, troponin levels may also be elevated because of conditions other than MI, such as myocarditis and renal failure. Moreover, the increased sensitivity of the cardiac troponin assay has inevitably come with reduced specificity.

With advances in diagnosis and clinical care of acute phase of MI, more than 70% of MI patients survive the acute hospital phase. Cardiac imaging adds critical value in the optimal clinical management of these patients by providing answers to the questions pertaining to cardiac remodeling, left ventricular function, presence of inducible ischemia, presence of dysfunctional viable myocardium, future risk of adverse events including risk of ventricular arrhythmias and heart failure, and the need for anticoagulation. High resolution imaging of necrotic myocardial tissue is of immense significance in these circumstances. As noted previously, prior to the present disclosure, there has been no agent available for PET imaging of MI. In the present work, we developed a method to synthesize $^{18}$F-labeled fluoroglucaric acid. As a proof of principal, we used $^{18}$F-FDG as our starting material to test the efficacy of $^{18}$F-FGA to delineate myocardial damage induced by isoproterenol (ISO) in a rat model. As is evident from increased cardiac troponin in plasma and altered ECG profile, ISO treatment results in significant cardiomyopathy. We also found a significant reduction in plasma corticosterone in ISO-treated rats, which corroborates the findings of increased clearance of corticosterone accompanied by its reduced serum protein-binding in ISO-induced MI.

Oxidation by nitric acid is the most widely used method for large-scale production of glucaric acid from glucose. However, this method provides yields of less than 50%, takes several hours to complete, and produces noxious fumes. Electrochemical oxidation is relatively clean, but in the absence of chemical catalysts the reaction has diminished yields and selectivity. Neither of these methods could thus be applied for quantitative and rapid synthesis of radiolabeled glucaric acid for PET. The present disclosure thus describes a novel method for producing radiolabeled glucaric acid, which in a non-limiting exemplary embodiment uses TEMPO and sodium hypochlorite (or calcium hypochlorite). TEMPO or TEMPO derivatives such as 4-acetamido-TEMPO are stable free radicals that selectively oxidize primary alcohols to aldehydes, and aldehydes to carboxylic acids. This method has been previously reported as an effective way of producing of glucaric acid from glucose in a reaction requiring controlled conditions of pH and temperature. It provides higher yields (85%) than the nitric acid-based oxidation, but comes with additional challenges. One of the difficulties of this reaction is the necessity to constantly monitor and maintain a basic pH (e.g., between about 11-11.6). In addition, the reaction has to take place at a temperature (e.g., <5° C.) which prevents excessive formation of side-products by over-oxidation of glucose. These drawbacks and the need of relatively expensive oxidizing agent TEMPO for oxidation meant limited utility of the method for large-scale production of glucaric acid. However, as discovered herein, this method was suited for the production of $^{18}$F-FGA from commercially available $^{18}$F-FDG.

Figure 5:
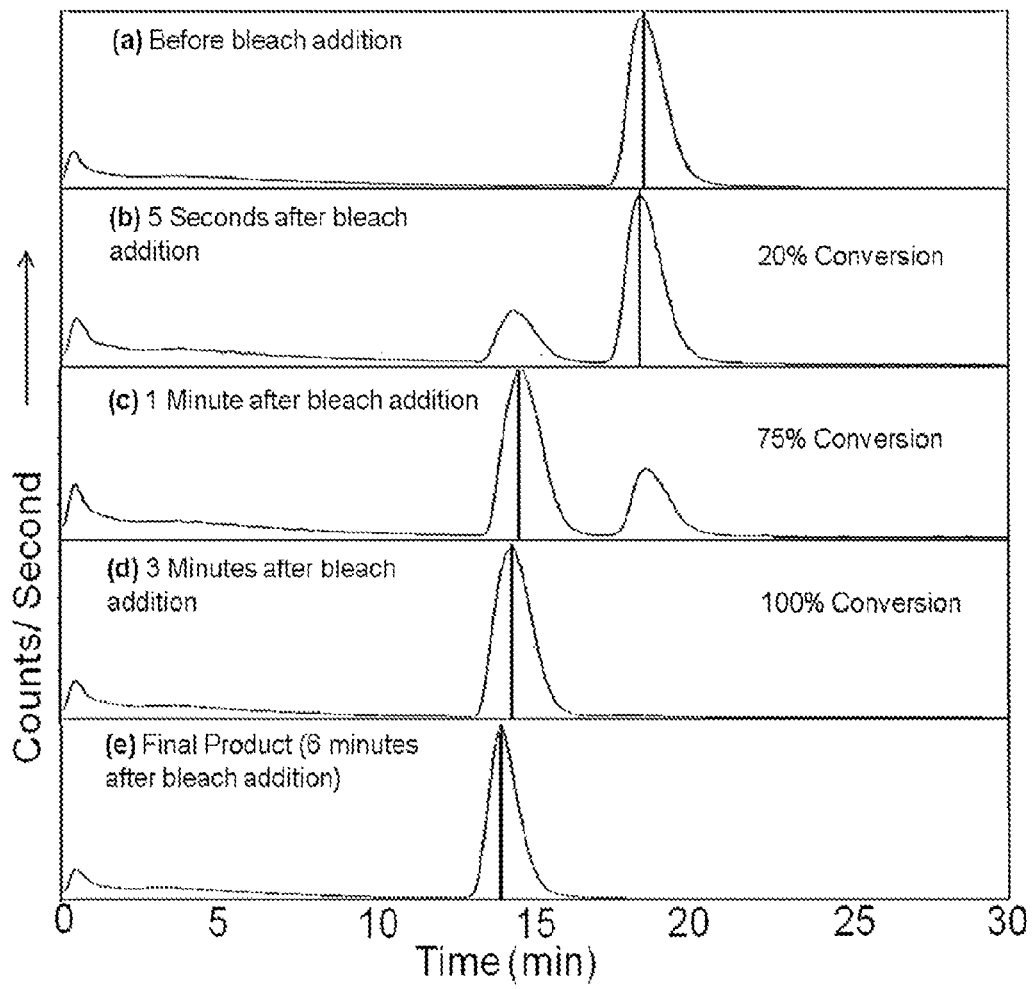
FIG. 5 shows Radio-HPLC time-dependency results of oxidation of $^{18}$F-FDG (F-18-FDG) to $^{18}$F-FGA (F-18-FGA) by an oxidizing agent after addition of a reaction initiator (bleach —NaOCl). (a) before initiation, (b) 5 seconds after initiation, (c) 1 minute after initiation, and (d) 3 minutes after initiation. Radio-HPLC of final purified $^{18}$F-FGA is shown in (e). $^{18}$F-FDG was entirely consumed within 3 min of the addition of bleach.

As the results of the present work indicate in at least one non-limiting embodiment, TEMPO-mediated oxidation of $^{18}$F-FDG in short-duration reactions at nano-scale levels can be effectively controlled by maintaining the temperature of reaction block by ice or other cooling means such as refrigeration, and buffering the reaction mixture with bicarbonate buffer. These modifications eliminated the need for continuous pH-monitoring of the reaction mixture and prevented over-oxidation of $^{18}$F-FDG. Post-optimization, in at least one embodiment, the present method takes approximately 5 min for substantially 100% conversion of precursor $^{18}$F-FDG into $^{18}$F-FGA (FIG. 5). The use of $^{18}$F-FDG as a precursor to produce $^{18}$F-FGA is innovative as it eliminates the need to deviate commercial production cycles in a cyclotron for creating a specialized product.

The present results of biodistribution in normal mice indicated that $^{18}$F-FGA was cleared from the body almost exclusively via the renal system, and there was negligible accumulation in any other organ. $^{18}$F-FDG on the other hand is known to accumulate in healthy heart, brain, and metabolically active tissues. The first phase of the biphasic kinetics of $^{18}$F-FGA clearance from blood was very rapid, as over 99% of the injected dose had left the blood within first 30 min of injection. These findings depict favorable characteristics of $^{18}$F-FGA for MI imaging. $^{18}$F-FGA does not significantly accumulate in normal heart and surrounding tissues and organs, especially the liver, and its rapid clearance from blood predicted high target/non-target ratio in MI.

In the rat model of ISO-induced MI, we found that $^{18}$F-FGA accumulation in ISO-treated hearts was quite rapid, within 1 h. The contrast increased when the rats were imaged at 4 h post-injection. Additionally, there was no detectable signal in normal heart during early or delayed imaging. There was substantial accumulation of $^{18}$F-FDG in normal heart versus that of $^{18}$F-FGA. $^{18}$F-FDG accumulation was reduced in ISO-treated hearts, but it was also detectable in surrounding tissues, including brown fat. These results are in accordance with the clinical and pre-clinical findings reported about $^{18}$F-FDG accumulation in cardiomyopathy. We suspect that the decrease in cardiac $^{18}$F-FDG accumulation in ISO treated rats is due to the inability of the necrotic areas to accumulate $^{18}$F-FDG. However, low doses of ISO have been shown to increase $^{18}$F-FDG uptake in brown fat and some tumor lines.

Additionally, $^{99m}$Tc-MIBI images were not able to clearly delineate myocardial pathology (FIG. 11). Since $^{99m}$Tc-MIBI is taken up by viable myocardial tissue, but not by necrotic tissue, we expected to see reduced uptake in the ISO treated hearts. However, the differential uptake between damaged and normal myocardium was not very conspicuous with this agent. Other groups have reported varying degree of alterations in MIBI uptake as a result of cardiotoxic agents and myopathies. MIBI uptake has been reported to increase in patients with doxorubicin induced cardiotoxicity.

No apparent changes in MIBI uptake were reported between controls and patients with statin induced myopathy. In one study, no difference in heart uptake ratios was seen between healthy patients and those with congestive heart failure. Because MIBI uptake is dependent on cellular integrity and mitochondrial viability, it is likely that uptake in conditions of cardiomyopathy are dependent on how the injury alters mitochondrial function. The damage created by ISO treatment is diffuse and widespread in the heart. In the absence of a focal area of necrosis, MIBI is apparently not able to provide differential diagnosis of ISO-induced tissue damage.

In contrast to $^{18}$F-FDG and $^{99m}$Tc-MIBI imaging, PET images of $^{18}$F-FGA clearly diagnosed ISO-induced cardiomyopathy in rats. Although the exact molecular target of $^{18}$F-FGA in injured cardiac tissue is not known, without wishing to be bound by theory, previous work with $^{99m}$Tc-glucarate suggests that it binds to nuclear histone proteins exposed during necrosis. Negatively-charged glucarate is unable to cross intact cell membranes to bind positively-charged histones, but the loss of membrane integrity in necrotic tissue allows glucarate to become intracellular.

As noted above, results show that $^{18}$F-FGA localizes in necroses caused by brain stroke (FIG. 13). $^{18}$F-FGA accumulates in stroke regions of ipsilateral cerebral hemisphere in a mouse model of middle cerebral artery occlusion. Corresponding perfusion images of HMPAO/SPECT show deficient uptake in stroke regions, but normal uptake in contralateral cerebral hemisphere.

The present work thus shows that using buffered oxidation conditions $^{18}$F-FGA can be synthesized by converting commercially available $^{18}$F-FDG. These conditions are conducive to rapid purification and processing to produce a clinically useful product without the need of dedicated precursor of $^{18}$F-FGA. Furthermore, we demonstrated the utility of $^{18}$F-FGA to image myocardial damage in a rat model of ISO-induced injury. $^{18}$F-FGA uptake was not detectable in hearts of healthy rats, but there was clear accumulation in ISO treated rats. As compared to FDG and MIBI, FGA is more clearly able to delineate between control and isoproterenol-induced myocardial injury in rats. Because of the profound impact of accurate and early detection of MI on patient care, definitive diagnosis is of critical importance. When compared to clinically used diagnostic agents such as $^{18}$F-FDG and $^{99m}$Tc-Sestamibi, $^{18}$F-FGA performed better in delineating healthy from damaged myocardium. Although controlled trials will further unravel the role of new PET agents for perfusion imaging (Flurpiridaz and BFPET), it is noteworthy that imaging of myocardial viability, as indicated by intact perfusion, has not always able to predict clinical outcome of revascularization or therapy in MI. The infarct-avid agent $^{18}$F-FGA disclosed herein will complement or supplant advances in perfusion imaging by PET. To the best of our knowledge, $^{18}$F-FGA is the first agent for directly imaging necroses by PET versus indirect imaging of necroses using perfusion agents.

In accordance with the foregoing, the present disclosure is directed to at least the following non-limiting embodiments:

Clause 1. In at least one embodiment the present disclosure includes an imaging agent comprising 2-deoxy-2-[$^{18}$F]fluoroglucaric acid ($^{18}$F-FGA), or a pharmaceutically-acceptable salt thereof.

Clause 2. A composition comprising the imaging agent of clause 1 disposed in a pharmaceutically-acceptable carrier, diluent, vehicle, or excipient.

Clause 3. A method of positron emission tomography (PET) imaging of a subject, comprising: administering to the subject an imaging agent comprising 2-deoxy-2-[$^{18}$F]fluoroglucaric acid ($^{18}$F-FGA), or a pharmaceutically-acceptable salt thereof; allowing the imaging agent to penetrate into a tissue of the subject, the tissue suspected to contain a necrosis; and collecting a PET image of the tissue suspected to contain the necrosis.

Clause 4. The method of clause 3, comprising preparing the $^{18}$F-FGA, or a pharmaceutically-acceptable salt thereof, from a quantity of 2-deoxy-2-[$^{18}$F]fluoro-D-glucose ($^{18}$F-FDG), wherein the administering step occurs within about 3 hours after preparing the $^{18}$F-FGA.

Clause 5. The method of clause 3 or 4, wherein the subject is suspected of having tissue damage due to a cancer, brain stroke, traumatic brain injury, or myocardial infarction.

Clause 6. The method of any one of clauses 3-5, wherein the tissue is selected from a group consisting of tissues of the myocardium, brain, breast, prostate, colon, kidney, spleen, limb, and lung.

Clause 7. The method of any one of clauses 3-6, wherein the imaging agent preferentially accumulates in the necrosis.

Clause 8. A method of preparing a radiopharmaceutical for use in PET imaging, comprising: combining a quantity of 2-deoxy-2-[$^{18}$F]fluoro-D-glucose ($^{18}$F-FDG) with an oxidizing agent, and an alkaline buffering agent to faun a reaction mixture; and reacting the reaction mixture for a duration of less than about 10 min causing conversion of substantially all of the $^{18}$F-FDG into 2-deoxy-2-[$^{18}$F]fluoroglucaric acid ($^{18}$F-FGA).

Clause 9. The method of clause 8, wherein the oxidizing agent is selected from the group consisting of 2,2,6,6-tetramethylpiperidine 1-oxyl (TEMPO), 4-hydroxy-TEMPO, TEMPO methacrylate, 4-Oxo-TEMPO, 4-amino-TEMPO, 4-acetamido-TEMPO, 4-carboxy-TEMPO, 4-hydroxy-TEMPO benzoate, 4-(2-Iodoacetamido)-TEMPO, 4-Maleimido-TEMPO, 4-Isothiocyanato-TEMPO, 4-(2-Bromoacetamido)-TEMPO, 4-methoxy-TEMPO, 4-Cyano-TEMPO, 4-amino-4-carboxy-TEMPO, 4-Phosphonooxy-TEMPO hydrate, 2,2,6,6-tetramethyl-4-(methylsulfonyloxy)-1-piperidinooxy, hydrogen peroxide, sodium hypochlorite, calcium hypochlorite, ozone, nitric acid, permanganate compounds, halogens, metal-catalyzed oxidation agents, gold nanoparticles, nanoparticles which mimic peroxidase activity-mimicking nanoparticles, glucose oxidase, and glucose-oxidizing enzymes or compounds.

Clause 10. The method of clause 8 or 9, wherein the alkaline buffering agent has a buffering capacity in a pH range of about 9 to about 12.

Clause 11. The method of any one of clauses 8-10, wherein the reacting step occurs at a reaction temperature in a range of about 0° C. to about 25° C.

Clause 12. The method of any one of clauses 8-11, comprising adding an acid to the reaction mixture after conversion of the $^{18}$F-FDG into $^{18}$F-FGA to change the pH of the reaction mixture to a pH in a range of about 6.5 to about 7.5.

Clause 13. The method of any one of clauses 8-12, wherein the oxidizing agent is a free compound, or is linked to a bead, resin, or polymer.

Clause 14. The method of any one of clauses 8-13, wherein the reaction mixture further comprises a reaction initiator.

Clause 15. The method of clause 14, wherein the reaction initiator is selected from the group consisting of sodium hypochlorite (NaOCl) and calcium hypochlorite (Ca(ClO)$_2$.

Clause 16. The method of any one of clauses 8-15, wherein the reaction mixture further comprises a reaction accelerator.

Clause 17. The method of clause 16, wherein the reaction accelerator is selected from the group consisting of sodium bromide (NaBr) and potassium bromide (KBr).

Clause 18. A kit for producing 2-deoxy-2-[$^{18}$F]fluoroglucaric acid ($^{18}$F-FGA), comprising: (1) an oxidizing agent, (2) a reaction initiator, (3) a reaction accelerator, and (4) an alkaline buffering agent; and instructions for combining a quantity of 2-deoxy-2-[$^{18}$F]fluoro-D-glucose ($^{18}$F-FDG) with the oxidizing agent, the reaction initiator, the reaction accelerator, and the buffering agent to produce the $^{18}$F-FGA.

Clause 19. The kit of clause 18, further comprising a container containing the $^{18}$F-FDG.

Clause 20. The kit of clause 18 or 19, wherein the oxidizing agent, reaction accelerator, and buffering agent are disposed in a first container, and the reaction initiator is disposed in a second container.

Clause 21. The kit of any one of clauses 18-20, wherein the oxidizing agent, reaction accelerator, buffering agent, and reaction initiator are disposed in separate containers.

Clause 22. The kit of any one of clauses 18-21, wherein the alkaline buffering agent has a buffering capacity in a range of about pH 9 to about pH 12.

Clause 23. The kit of any one of clauses 18-22, further comprising an acid able to neutralize the reaction mixture to a pH in a range of about 6.5 to 7.5.

Clause 24. The kit of any one of clauses 18-23, wherein the oxidizing agent is selected from the group consisting of 4-hydroxy-TEMPO, TEMPO methacrylate, 4-Oxo-TEMPO, 4-amino-TEMPO, 4-acetamido-TEMPO, 4-carboxy-TEMPO, 4-hydroxy-TEMPO benzoate, 4-(2-Iodoacetamido)-TEMPO, 4-Maleimido-TEMPO, 4-Isothiocyanato-TEMPO, 4-(2-Bromoacetamido)-TEMPO, 4-methoxy-TEMPO, 4-Cyano-TEMPO, 4-amino-4-carboxy-TEMPO, 4-Phosphonooxy-TEMPO hydrate, 2,2,6,6-tetramethyl-4-(methylsulfonyloxy)-1-piperidinooxy, hydrogen peroxide, sodium hypochlorite, calcium hypochlorite, ozone, nitric acid, permanganate compounds, halogens, metal-catalyzed oxidation agents, gold nanoparticles, nanoparticles which mimic peroxidase activity-mimicking nanoparticles, glucose oxidase, and glucose-oxidizing enzymes or compounds.

Clause 25. The kit of any one of clauses 18-24, wherein the reaction initiator is selected from the group consisting of sodium hypochlorite (NaOCl) and calcium hypochlorite (Ca(ClO)$_2$.

Clause 26. The kit of any one of clauses 18-25, wherein the reaction accelerator is selected from the group consisting of sodium bromide (NaBr) and potassium bromide (KBr).

Clause 27. The kit of any one of clauses 18-26, wherein the oxidizing agent is a free compound, or is linked to a bead, resin, or polymer.

Clause 28. The kit of any one of clauses 18-27, wherein the instructions are provided as a package insert.

Clause 29. The kit of any one of clauses 18-28, wherein the instructions are accessible virtually by a user of the kit via a uniform resource locator (URL) or web address.

Clause 30. The kit of any one of clauses 18-29, wherein the instructions comprise directions for administering the $^{18}$F-FGA to a subject.

Clause 31. The kit of any one of clauses 18-30, comprising at least one thin layer chromatography (TLC) strip.

Clause 32. The kit of any one of clauses 18-31, comprising a TLC solvent.

While the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the inventive concepts of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the present disclosure. Changes may be made in the formulation of the various compositions described herein, the methods described herein or in the steps or the sequence of steps of the methods described herein without departing from the spirit and scope of the present disclosure. Further, while various embodiments of the present disclosure have been described in claims herein below, it is not intended that the present disclosure be limited to these particular claims.

What is claimed is:

1. A process for preparing a radiopharmaceutical composition, comprising:
combining a quantity of 2-deoxy-2-[$^{18}$F]fluoro-D-glucose ($^{18}$F-FDG) with an oxidizing agent, a reaction accelerator, and an alkaline buffering agent to form a first mixture;
adding a reaction initiator to the first mixture to form a reaction mixture; and
incubating the reaction mixture, wherein substantially all of the $^{18}$F-FDG is converted into 2-deoxy-2-[$^{18}$F]fluoroglucaric acid ($^{18}$F-FGA) in less than about 10 minutes after adding the reaction initiator, and wherein the conversion of $^{18}$F-FDG into $^{18}$F-FGA occurs without monitoring and adjusting the pH of the reaction mixture, thereby preparing the radiopharmaceutical composition and, after conversion of the $^{18}$F-FDG into $^{18}$F-FGA, adding an acid to the reaction mixture to change the pH of the reaction mixture to a pH in a range of about 6.5 to about 7.5.

2. The process of claim 1, wherein the oxidizing agent is selected from the group consisting of 2,2,6,6-tetramethylpiperidine 1-oxyl (TEMPO), 4-hydroxy-TEMPO, TEMPO methacrylate, 4-oxo-TEMPO, 4-amino-TEMPO, 4-acetamido-TEMPO, 4-carboxy-TEMPO, 4-hydroxy-TEMPO benzoate, 4-(2-iodoacetamido)-TEMPO, 4-maleimido-TEMPO, 4-isothiocyanato-TEMPO, 4-(2-bromoacetamido)-TEMPO, 4-methoxy-TEMPO, 4-cyano-TEMPO, 4-amino-4-carboxy-TEMPO, 4-phosphonooxy-TEMPO hydrate, 2,2,6,6-tetramethyl-4-(methylsulfonyloxy)-1-piperidinooxy, hydrogen peroxide, sodium hypochlorite, calcium hypochlorite, ozone, nitric acid, permanganate compounds, halogens, metal-catalyzed oxidation agents, gold nanoparticles, nanoparticles which mimic peroxidase activity-mimicking nanoparticles, glucose oxidase, and glucose-oxidizing enzymes or compounds.

3. The process of claim 1, wherein the alkaline buffering agent has a buffering capacity in a pH range of about 9 to about 12.

4. The process of claim 1, wherein the incubating step occurs at a reaction temperature in a range of about 0° C. to about 25° C.

5. The process of claim 1, wherein the oxidizing agent is a free compound, or is linked to a bead, resin, or polymer.

6. The process of claim 1, wherein the reaction initiator is selected from the group consisting of sodium hypochlorite and calcium hypochlorite and the reaction accelerator is selected from the group consisting of sodium bromide and potassium bromide.

7. The process of claim 1, wherein the alkaline buffering agent is a bicarbonate buffer.

8. The process of claim 7, wherein the bicarbonate buffer is sodium bicarbonate.

* * * * *